United States Patent [19]

Yerich et al.

[11] Patent Number: 5,562,711
[45] Date of Patent: Oct. 8, 1996

[54] METHOD AND APPARATUS FOR RATE-RESPONSIVE CARDIAC PACING

[75] Inventors: Charles G. Yerich, Fridley; William J. Combs, Eden Prairie; Karen J. Kleckner, New Brighton; Eric J. Panken, Minneapolis; Richard S. Schallhorn, St. Paul; John D. Wahlstrand, Shoreview, all of Minn.

[73] Assignee: Medtronic, Inc., Minneapolis, Minn.

[21] Appl. No.: 346,813

[22] Filed: Nov. 30, 1994

[51] Int. Cl.⁶ ............................................. A61N 1/365
[52] U.S. Cl. ...................................... 607/17; 607/18
[58] Field of Search ........................................ 607/17, 18

[56] References Cited

U.S. PATENT DOCUMENTS

| | | | |
|---|---|---|---|
| 4,374,382 | 2/1983 | Markowitz | 607/27 |
| 4,476,868 | 10/1984 | Thompson | 607/14 |
| 4,485,813 | 12/1984 | Anderson | 607/122 |
| 4,527,568 | 7/1985 | Rickards | 607/18 |
| 4,556,063 | 12/1985 | Thompson | 607/32 |
| 4,688,573 | 8/1987 | Alt | 607/21 |
| 4,702,253 | 10/1987 | Nappholz | 607/20 |
| 4,719,920 | 1/1988 | Alt | 607/21 |
| 4,721,110 | 1/1988 | Lampadius | 607/20 |
| 4,722,342 | 2/1988 | Amundson | 607/19 |
| 4,782,836 | 11/1988 | Alt | 607/19 |
| 4,884,576 | 12/1989 | Alt | 607/18 |
| 4,966,146 | 10/1990 | Webb | 607/19 |
| 4,972,834 | 11/1990 | Begemann | 607/25 |
| 5,052,388 | 10/1991 | Sivula | 607/22 |
| 5,063,927 | 11/1991 | Webb | 607/18 |
| 5,065,759 | 11/1991 | Begemann | 607/18 |
| 5,101,824 | 4/1992 | Lekholm | 607/18 |
| 5,127,404 | 7/1992 | Wyborny | 607/32 |
| 5,154,170 | 10/1992 | Bennett | 607/17 |
| 5,197,467 | 3/1993 | Steinhaus et al. | 607/20 |
| 5,271,395 | 12/1993 | Wahlstrand | 607/9 |
| 5,312,453 | 5/1994 | Shelton | 607/9 |
| 5,330,513 | 7/1994 | Nichols et al. | 607/17 |
| 5,376,106 | 12/1994 | Stahmann et al. | 607/18 |
| 5,387,229 | 2/1995 | Poore | 607/18 |
| 5,441,524 | 8/1995 | Rueter et al. | 607/18 |

*Primary Examiner*—William E. Kamm
*Assistant Examiner*—Carl H. Layno
*Attorney, Agent, or Firm*—Michael B. Atlass; Harold R. Patton

[57] ABSTRACT

A body-implantable rate-responsive cardiac pacemaker is provided with circuitry for sensing a plurality of physiologic parameters known to be indicative of a patient's metabolic demand for increased cardiac output. In one embodiment, a rate-responsive pacemaker is provided with an activity sensor for detecting the patient's level of physical activity, and is further provided with an impedance sensing circuit for detecting the patient's level of minute ventilation by monitoring cardiac impedance. A rate-response transfer function, implemented by the pacemaker's control circuitry, periodically computes a rate-responsive pacing rate as a function of the outputs from both physiologic sensing circuits. The pacemaker's pacing rate is variable within a rate range defined by predetermined (programmable) upper and lower limits. In the preferred embodiment, the influence of activity sensing and minute ventilation parameters varies in accordance with the current pacing rate. In particular, the influence of activity sensing in rate determination in accordance with the rate-response function is greater than that of minute ventilation, for slower pacing rates, while the influence of minute ventilation sensing dominates over that of activity sensing for higher pacing rates. Rate response operation of the disclosed system is recorded in the form of histogram data stored over a predetermined history time. The relative influence of the activity sensing and minute ventilation sensing on rate determination is periodically scaled or balanced based upon comparison of the histogram data with predetermined desired response data.

18 Claims, 5 Drawing Sheets

METHOD AND APPARATUS FOR RATE-RESPONSIVE CARDIAC PACING

FIELD OF THE INVENTION

This invention relates generally to the field of automatic, body-implantable cardiac pacemakers, and more particularly to a method and apparatus for performing rate-responsive cardiac pacing.

BACKGROUND OF THE INVENTION

In general, cardiac pacemakers are electrical devices used to supplant some or all of an abnormal heart's natural pacing function. Pacemakers typically operate to deliver appropriately timed electrical stimulation signals, sometimes called pacing pulses, designed to cause the myocardium to contract or "beat." For state-of-the-art pacemakers, the rate at which stimulation signals are delivered may be variable, and such variation may occur automatically in response to detected changes in a patient's level of physical activity. Such rate- or activity-responsive pacemakers depend on physiologically-based signals, such as signals from sensors which measuring naturally-occurring (intrinsic) cardiac electrical activity, or which measure the pressure inside the patient's ventricle. Such physiologically-based signals provide information regarding cardiac function and the need for pacemaker intervention, and thus are useful for determining a patient's metabolic demand for oxygenated blood.

One popular method for measuring a patient's demand for oxygenated blood is to monitor the patient's level of physical activity by means of a piezoelectric, microphone-like transducer. A pacemaker which employs such a method is disclosed in U.S. Pat. No. 4,485,813 to Anderson et al.

In typical prior art rate-responsive pacemakers, the pacing rate is determined according to the output from an activity sensor. The pacing rate is variable between a predetermined maximum and minimum level, which may be selectable by a physician from among a plurality of programmable upper and lower rate limit settings. When the activity sensor output indicates that the patient's activity level has increased, the pacing rate is increased from the programmed lower rate by an incremental amount which is determined as a function of the output of the activity sensor. That is, the rate-responsive or "target" pacing rate in a rate-responsive pacemaker is determined as follows:

TargetRate=ProgrammedLowerRate+f (SensorOutput)

where f is typically a linear or monotonic function of the sensor output. As long as patient activity continues to be indicated, the pacing rate is periodically increased by incremental amounts until the rate computed according to the above formula is reached (or until the programmed upper rate limit is reached, whichever is lower). In this way, an elevated pacing rate (i.e., one higher than the programmed lower rate limit) may be sustained during periods of patient activity. When patient activity ceases, the pacing rate is gradually reduced, until the programmed lower rate limit is reached.

For any of the known rate-responsive pacemakers, it is clearly desirable that the sensor output correlate to as high a degree as possible with the actual metabolic and physiologic needs of the patient, so that the resulting rate-responsive pacing rate may be adjusted to appropriate levels. A piezoelectric activity sensor can only be used to indirectly determine the metabolic need. The physical activity sensed by a piezoelectric transducer may in some cases be influenced by upper body motion. Therefore, an exercise that involves arm motion may provide signals that are inappropriately greater than the metabolic need. Conversely, exercises that stimulate the lower body only, such as bicycle riding, may provide a low indication of metabolic need while the actual requirement is higher.

To address these perceived disadvantages in the prior art, it has been proposed to utilize other physiologically-based parameters in assessment of a patient's metabolic demand. Minute ventilation ($V_E$) has been demonstrated clinically to be a parameter that correlates directly to the actual metabolic and physiologic needs of the patient. Minute ventilation is defined by the equation:

$$V_E = RR \times TV$$

where RR=respiration rate in breaths per minute, and TV=tidal volume in liters. Clinically, the measurement of $V_E$ is performed by having the patient breathe directly into a device that measures the exchange of air and computing the total volume per minute. The direct measurement of $V_E$ is not practical with an implanted device. However, measurement of the impedance changes of the thoracic cavity can be implemented with an implanted pacemaker, and transthoracic cardiac impedance has been shown to correlate well with $V_E$. A pacemaker that is provided with impedance measurement capabilities is disclosed in U.S. Pat. No. 4,702,253 issued to Nappholz et al. on Oct. 27, 1987. The magnitude of the change of the impedance signal corresponds to the tidal volume and the frequency of change corresponds to respiration rate. Thus, measurement of cardiac impedance can be used as one method for obtaining $V_E$ data.

In practice, cardiac impedance can be measured through assessment of the impedance present between two or more cardiac electrodes, such as the electrodes otherwise used for pacing and/or sensing in connection with a cardiac pacemaker. In particular, it has been shown that cardiac impedance can be measured by delivering constant-current excitation pulses between two "source" electrodes, such that the current is conducted through some region of cardiac tissue. The voltage differential between two "recording" electrodes can then be measured to ascertain the impedance as reflected by the voltage differential arising from the conduction of the excitation current pulses through the tissue. Such an impedance measuring technique has proven to be practicable in connection with implantable devices, such as cardiac pacemakers.

In U.S. Pat. No. 4,721,110 to Lampadius, there is described a rheographic arrangement for a cardiac pacemaker in which the base pacing rate of the pacemaker is determined, in part, by a rheographically derived respiration rate signal.

Correlation of breathing and intrathoracic pressure fluctuations with impedance of blood in the heart is also recognized in U.S. Pat. No. 4,884,576 to Alt, which describes the measurement of impedance between two electrodes. According to the Alt '576 patent, low-pass filtering of the impedance signal yields a signal from which the patient's respiratory rate can be derived, while high-pass filtering of the same signal yields a signal from which the patient's cardiac function can be observed.

There are currently several commercially-available implantable devices which employ rheographic techniques to adjust the pacing rate in response to metabolic needs. For example, the Biorate device manufactured by Biotec International, Bologna, Italy, uses a bipolar rheographic arrangement to monitor the patient's respiration rate. The Meta-MV device manufactured by Telectronics, Inc., Englewood, Colo., uses a tripolar rheographic arrangement to monitor the patient's metabolic demand for oxygenated blood. The Precept device manufactured by CPI, St. Paul, Minn., uses a tetrapolar rheographic configuration to monitor the patient's pre-ejection interval (PEI), stroke volume, and heart tissue contractility.

The Legend Plus™ pulse generator, manufactured by Medtronic, Inc., Minneapolis, Minn. and currently undergoing clinical trials in the United States is another example of an implantable pacemaker which employs rheography in support of its rate-response function. The Legend Plus™ delivers a biphasic excitation signal between the pulse generator's canister (serving as an indifferent electrode) and a ring electrode of a transvenous pacing/sensing lead. Impedance sensing in the Legend Plus™ is carried out between the lead's tip electrode and the pulse generator canister. The Legend Plus™ impedance measuring circuitry generates an impedance waveform in which both respiration and cardiac systole are reflected. This waveform is used by the pacemaker's circuitry to derive a minute ventilation value $V_E$, as defined above. The Legend Plus™ periodically assesses a patient's $V_E$, and adjusts its base pacing rate up or down in accordance with the metabolic demand reflected in the $V_E$ value. (Various aspects of the Legend Plus™ device are described in greater detail in U.S. Pat. No. 5,271,395 to Wahlstrand et al, entitled "Method and Apparatus for Rate-Responsive Cardiac Pacing," commonly assigned to the assignee of the present invention and hereby incorporated by reference herein in its entirety.)

Another disclosure which relates to the use of rheography in connection with an implanted device can be found in co-pending U.S. patent application Ser. No. 08/233,901 filed on Apr. 28, 1994 in the name of Wahlstrand et al. entitled "Method and Apparatus for Sensing of Cardiac Function", which proposes a method and apparatus for obtaining an impedance waveform. The Wahlstrand et al. application, which relates to the use of a specialized lead for improving the quality of an impedance waveform like that utilized in the aforementioned Legend Plus™, is hereby incorporated by reference herein in its entirety.

Yet another disclosure relating to the use of rheography in connection with implantable devices can be found in co-pending U.S. patent application Ser. No. 08/277,051 filed on Jul. 19, 1994 in the name of Gianni Plicchi et al. entitled "Time-Sharing Multi-Polar Rheography".

As noted above, the utilization of a piezoelectric transducer in a cardiac pacemaker provides a useful but only an indirect indication of a patient's actual level of physical activity, and thus allows for the possibility of false positive or false negative indications of elevated levels of a patient's metabolic demand. The above-noted problem associated with upper body movement is one example of this.

Similarly, the measurement of intracardiac impedance using rheographic techniques provides a useful but somewhat indirect indication of a patient's respiration and cardiac rates, and therefore also allows for the possibility of error in determining a patient's metabolic need. It has been shown that the use of transthoracic impedance to indicate minute ventilation levels has the potential for false positive indications of elevated metabolic demand levels, due to upper body myopotential interference and postural changes. Furthermore, slow-acting physiologic parameters such as transitory blood chemistry changes can also impact impedance measurement.

In addition, basing pacing rate solely on minute ventilation measurements does not always provide an optimum pacing rate increase at the onset of exercise. Tidal volume (TV) and respiration rate (RR) levels have an inherent physiological time delay due to the response of the $CO_2$ receptors and the autonomic nervous system. An increase in $V_E$ can lag behind the need for increased cardiac output.

On the other hand, activity signals derived from a piezoelectric transducer do not typically exhibit this same time delay phenomenon at the onset of exercise. Moreover, minute ventilation signals derived from transthoracic impedance measurements tend to be more appropriately proportional to a wider variety of types of exercise (e.g., bicycling, walking, running, etc...) than piezoelectric sensor signals tend to be. In this regard, piezoelectric activity signals and transthoracic impedance measurements are mutually complementary in their efficacy in establishing a patient's level of metabolic demand. That is, the potential limitations of each type of sensing are different. This suggests that a combination of activity sensing using a piezoelectric transducer and minute ventilation sensing using rheographic techniques would provide an improved method of accurately tracking a patient's level metabolic demand.

SUMMARY OF THE INVENTION

In view of the foregoing considerations, the present invention is directed to an improved method and apparatus for implementing rate-responsive cardiac pacing in a body-implantable pulse generator system.

In particular, the present invention relates to a pacemaker which utilizes both impedance measurement and activity sensing in its determination of a variable pacing rate which increases or decreases in response to perceived changes in a patient's physiologic demand.

In accordance with one aspect of the invention, the pacemaker's impedance sensing circuitry and (piezoelectric transducer-based) activity sensing circuitry can be separately and independently enabled and disabled. If either sensing circuit is disabled, the pacemakers rate-response transfer function (i.e., its rate-response behavior) is based solely upon the enabled sensor. When both sensing circuits are enabled, however, the rate-response transfer function is based upon a combined or "blended" activity signal which represents contributions from both the activity sensing circuitry and the impedance (minute ventilation) sensing circuitry.

In accordance with another aspect of the present invention, the blending of output signals from the impedance and activity sensing subsystems of the pacemaker is performed in such a manner as to yield a combination signal in which the relative contributions of the activity and impedance signals varies as a function of the current "sensor rate" (where sensor rate as used herein refers to the varying pacing rate of the pacemaker operating in a rate-responsive mode). In particular, in the preferred embodiment of the invention the contribution of the activity sensor output signal dominates in the calculation of a sensor rate value for pacing rates at or near the lower end of the pacemaker's pacing rate range, while the impedance sensor output signal dominates in the calculation of a sensor rate at high pacing rates.

In accordance with yet another aspect of the invention, it is believed that the arrangement disclosed herein can be adapted to facilitate the combining or "blending" of outputs from different types of sensors (i.e., sensors other than impedance and activity sensors) which provide some indication of a patient's metabolic demand. For example, it is contemplated that the principles of the present invention may be applied to any dual-sensing pacemaker, i.e, any pacemaker capable of some combination of activity sensing, minute ventilation sensing, oxygen saturation sensing, pressure sensing, Q–T interval sensors and the like. The outputs of such sensors can be combined, in accordance with the present invention, in various combinations, such as in a pacemaker having both activity and Q–T sensing capabilities, oxygen saturation and minute ventilation sensing capabilities, etc.

BRIEF DESCRIPTION OF THE DRAWINGS

The foregoing and other aspects and features of the present invention can be better appreciated with reference to a detailed description of a specific embodiment of the invention, when read in conjunction with the accompanying drawings, wherein.

DETAILED DESCRIPTION OF A SPECIFIC EMBODIMENT OF THE INVENTION

GENERAL DESCRIPTION

Figure 1:
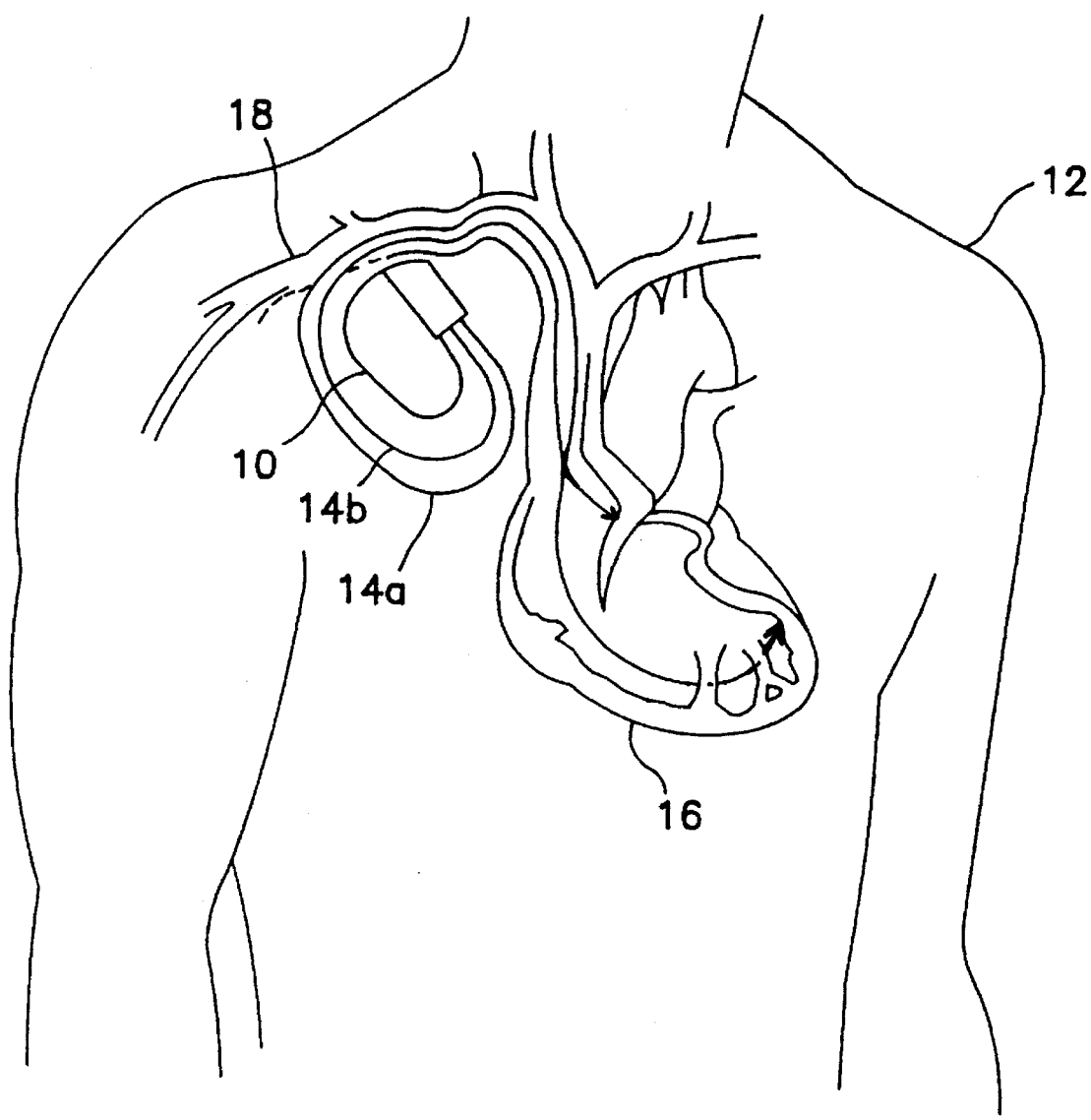
FIG. 1 is an illustration of a pacemaker in accordance with the present invention having been implanted into a human patient.

Referring to FIG. 1, there is shown an illustration of generally where a pacemaker 10 in accordance with one embodiment of the invention may be implanted in a patient 12. In accordance with conventional practice in the art, pacemaker 10 is housed within a hermetically sealed, biologically inert outer canister, which may itself be conductive and thus serve as an indifferent electrode in the pacemaker's pacing/sensing circuit. One or more pacemaker leads, collectively identified with reference numerals 14a (ventricular) and 14b (atrial) in FIG. 1 are electrically coupled to pacemaker 10 in a conventional manner, extending into the patient's heart 16 via a vein 18. Disposed generally near the distal end of leads 14a and 14b are one or more exposed conductive electrodes for receiving electrical cardiac signals and/or for delivering electrical pacing stimuli to heart 16. As will be appreciated by those of ordinary skill in the art, leads 14a and 14b may be implanted with its distal end situated in either the atrium or ventricle of heart 16.

Figure 2:
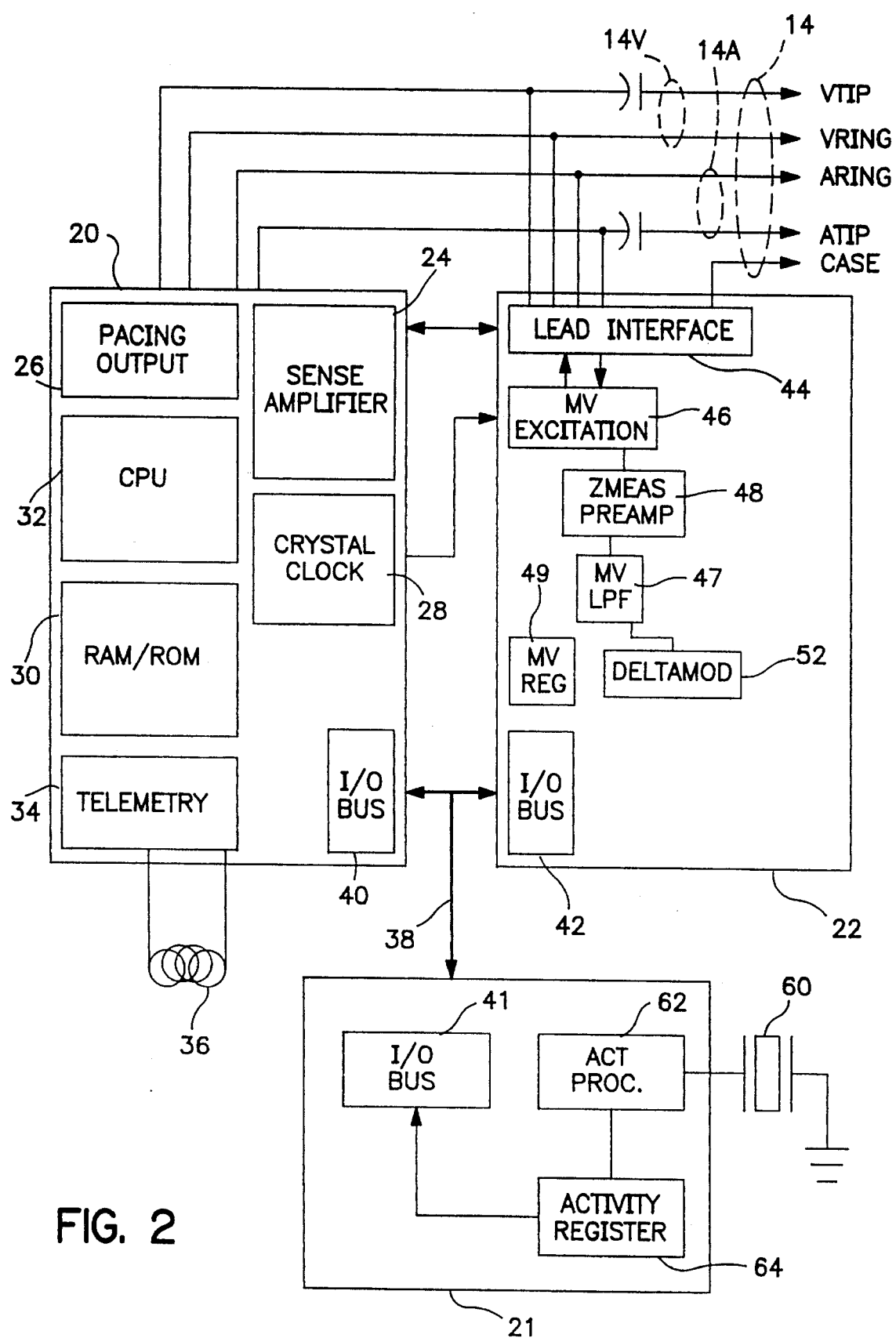
FIG. 2 is a block diagram illustrating the functional components of the pacemaker from FIG. 1.

Turning now to FIG. 2, there is shown a block diagram of the electronic circuitry which makes up pacemaker 10 in accordance with the presently disclosed embodiment of the invention. As can be seen from FIG. 2, pacemaker 10 comprises a primary pacing/control circuit 20, an activity sensor circuit 21, and a minute ventilation circuit 22. Much of the circuitry associated with pacing control circuit 20 is of conventional design, in accordance, for example, with what is disclosed in U.S. Pat. No. 5,052,388 to Sivula et al, entitled "Method and Apparatus for Implementing Activity Sensing in a Pulse Generator." The Sivula et al. '388 patent is hereby incorporated by reference herein in its entirety. To the extent that certain components of pacemaker 10 are purely conventional in their design and operation, such components will not be described herein in detail, as it is believed that design and implementation of such components would be a matter of routine to those of ordinary skill in the art. For example, pacing/control circuit 20 in FIG. 2 includes sense amplifier circuitry 24, pacing output circuitry 26, a crystal clock 28, a random-access memory and read-only memory (RAM/ROM) unit 30, a central processing unit (CPU) 32, and a telemetry circuit 34, all of which are well-known in the art.

Pacemaker 10 preferably includes internal telemetry circuit 34 so that it is capable of being programmed by means of external programmer/control unit 17 (shown in FIG. 1). Programmers and telemetry systems suitable for use in the practice of the present invention have been well known for many years.

Known programmers typically communicate with an implanted device via a bi-directional radio-frequency telemetry link, so that the programmer can transmit control commands and operational parameter values to be received by the implanted device, and so that the implanted device can communicate diagnostic and operational data to the programmer. Programmers believed to be suitable for the purposes of practicing the present invention include the Model 9760 and Model 9790 Programmers, commercially-available from Mealtronic, Inc., Minneapolis, Minn. Various telemetry systems for providing the necessary communications channels between an external programming unit and an implanted device have been developed and are well-known in the art. Telemetry systems believed to be suitable for the purposes of practicing the present invention are disclosed, for example, in the following U.S. Patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and are each hereby incorporated by reference herein in their respective entireties.

Typically, telemetry systems such as those described in the above-referenced patents are employed in conjunction with an external programming/processing unit. One programmer for non-invasively programming a cardiac pacemaker is described in the above-referenced Hartlaub et al. '884 patent.

Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modelled as an air-core coupled transformer. An example of such a telemetry system is shown in the above-referenced Thompson et al. '063 patent.

In order to communicate digital data using RF telemetry, a digital encoding scheme such as is described in the above-reference Wyborny et al. '404 patent can be used. In particular, for downlink telemetry a pulse interval modulation scheme may be employed, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encodes a digital "0" bit while a longer interval encodes a digital "1" bit.

For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen position data frame may be defined, wherein a pulse in one of the time slots represents a unique four bit portion of data.

As depicted in FIG. 1, programming units such as the above-referenced Mealtronic Model 9760 and 9790 programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

With continued reference to FIG. 2, pacemaker 10 is coupled to leads 14 which, when implanted, extend transvenously between the implant site of pacemaker 10 and the patient's heart 16, as previously noted with reference to FIG. 1. For the sake of clarity, the connections between leads 14 and the various components of pacemaker 10 are not shown in FIG. 2, although it will be clear to those of ordinary skill in the art that, for example, leads 14 will necessarily be coupled, either directly or indirectly, to sense amplifier circuitry 24 and pacing output circuit 26, in accordance with common practice, such that cardiac electrical signals may be conveyed to sensing circuitry 24, and pacing pulses may be delivered to cardiac tissue, via leads 14.

In the presently disclosed embodiment, two leads are employed—an atrial lead 14A having atrial tip and ring electrodes (ATIP and ARING in FIG. 2), and a ventricular lead 14V having ventricular tip and ring electrodes (VTIP and VRING in FIG. 2). In addition, as noted above, the conductive hermetic canister of pacemaker 10 serves as an indifferent electrode (CASE in FIG. 2).

As previously noted, pace/control circuit 20 includes central processing unit 32 which may be an off-the-shelf programmable microprocessor or microcontroller, but in the presently preferred embodiment of the invention is a custom integrated circuit. Although specific connections between CPU 32 and other components of pace/control circuit 20 are not shown in FIG. 2, it will be apparent to those of ordinary skill in the art that CPU 32 functions to control the timed operation of pacing output circuit 26 and sense amplifier circuit 24 under control of programming stored in RAM/ROM unit 30. It is believed that those of ordinary skill in the art will be familiar with such an operative arrangement.

With continued reference to FIG. 2, crystal oscillator circuit 28, in the presently preferred embodiment a 32,768-Hz crystal controlled oscillator, provides main timing clock signals to pace/control circuit 20 and to minute ventilation circuit 22.

It is to be understood that the various components of pacemaker 10 depicted in FIG. 2 are powered by means of a battery (not shown) which is contained within the hermetic enclosure of pacemaker 10, in accordance with common practice in the art. For the sake of clarity in the FIGURES, the battery and the connections between it and the other components of pacemaker 10 are not shown.

Pacing output circuit 26, which functions to generate pacing stimuli under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits which would be suitable for the purposes of practicing the present invention.

As shown in FIG. 2, pace/control circuit 20 is coupled to activity sensor circuit 21 and minute ventilation circuit 22 by means of multiple signal lines, designated collectively as 38 in FIG. 2. An I/O interface 40 in pace/control circuit 20, a corresponding I/O interface 41 in activity sensor circuit 21, and a corresponding I/O interface 42 in minute ventilation circuit 22, coordinate the transmission of signals between the three units.

MINUTE VENTILATION SENSING

Minute ventilation circuit 22 measures changes in transthoracic impedance, which has been shown to be proportional to minute ventilation. As noted above, minute ventilation is the product of tidal volume and respiration rate, and as such is a physiologic indicator of changes in metabolic demand and hence identifies the need to increase or decrease the heart rate.

Pacemaker 10 in accordance with the presently disclosed embodiment of the invention measures transthoracic impedance using a bipolar lead 14 and a tripolar measurement system. As will be hereinafter described in greater detail, minute ventilation circuit 22 delivers 30-μSec biphasic current excitation pulses of 1-mA (peak-to-peak) between a PING electrode of bipolar lead 14 and the conductive canister of pacemaker 10, functioning as an indifferent electrode CASE, at a rate of 16-Hz. The resulting voltage is then measured between a TIP electrode of lead 14 and the pacemaker CASE electrode. Such impedance measurement can be programmed to take place in either the atrium or ventricle of the patient's heart.

Figure 3:
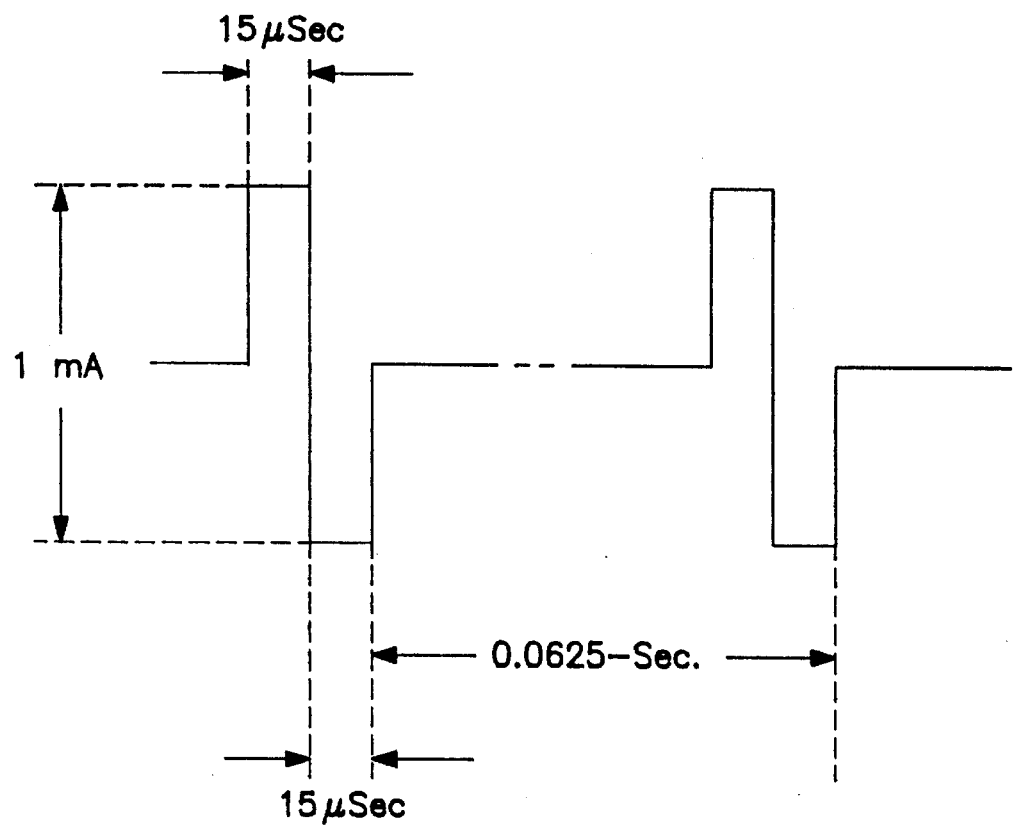
FIG. 3 is an illustration of a excitation current pulse delivered by impedance measurement circuitry in the pacemaker of FIG. 2.

An illustration of a biphasic excitation pulse delivered for impedance measurement in accordance with the present embodiment of the invention is shown in FIG. 3. It is believed that the biphasic nature of an excitation pulse, such as the one depicted in FIG. 3, offers the advantages over a monophasic pulse that the peak amplitude of the excitation pulse is minimized given the overall energy content of the pulse, electrode polarization is canceled, and DC current is balanced to avoid long-term lead metal-ion oxidation. As shown in FIG. 3, each phase of the biphasic pulse lasts for approximately 15-μSec, and the pulses are delivered once every 0.0625-Sec (i.e., at a rate of 16-Hz, as previously noted).

The impedance signal derived by minute ventilation circuit 22 has three main components: a DC offset voltage; a cardiac component resulting from the heart's function; and a respiratory component. The frequency of the cardiac and respiratory components are assumed to be identical to their physiologic origin. Since the respiratory component of the impedance signal derived by minute ventilation circuit 22 is of primary interest for the purposes of the present invention, the impedance signal is subjected to filtering in minute ventilation low-pass filter (MV LPF) 47 having a passband of 0.05- to 0.8-Hz (corresponding to 3–48 breaths per minute) to remove the DC and cardiac components.

A delta-modulator circuit 52 and counter are used to perform a respiration rate times peak-to-peak amplitude (tidal volume) function on the bandpass-filtered signal. The values generated by the delta-modulator counter, which are proportional to minute ventilation, are accumulated in an MV Data Register 49. The MV Data Register value can increase at a rate of 1 least-significant bit (LSB) every 2-mSec to a programmable value less than or equal to $(190)_X$ (the subscript "X" denoting a hexadecimal value). This $(190)_X$ value corresponds to a 600-Ω (peak-to-peak) change per minute in the impedance. The value in the MV Data Register is updated every two seconds, and thus becomes the MV input in the rate response algorithm, to be hereinafter described in greater detail.

With reference to FIG. 2, minute ventilation circuit 22 includes a lead interface circuit 44 which is essentially a multiplexer that functions to selectively couple and decouple minute ventilation circuit 22 to the VTIP, VRING, ATIP, ARING, and CASE electrodes, as will be hereinafter described in greater detail.

Coupled to lead interface circuit 44 is a minute ventilation excitation (MV EXCITATION) circuit 46 which functions to deliver the biphasic constant-current pulses between various combinations of lead electrodes (VTIP, VRING, etc. . . ) for the purpose of measuring cardiac impedance. In particular, MV EXCITATION circuit 46 delivers biphasic excitation pulses of the type delivered by the above-noted Legend Plus™ device, and in accordance with the method and apparatus described in the U.S. Pat. No. 5,271,395 to Wahlstrand et al., which is commonly assigned to the assignee of the present invention and hereby incorporated by reference herein in its entirety.

The electrodes between which the excitation pulses are delivered will vary depending upon whether atrial or ventricular impedance is being evaluated. The selection of the electrodes is made by lead interface circuit 44, under control of signals asserted by pace/control circuit 20 and conveyed to minute ventilation circuit 22 over bus 38. As noted above, minute ventilation measurements can be programmed to occur in either chamber of the heart. For ventricular-based minute ventilation evaluation, for example, biphasic pulses may be delivered at a rate of 16-Hz between the ventricular ring electrode VRING and the pacemaker canister CASE. Similarly, for atrial minute ventilation evaluation, the pulses may be delivered between the atrial ring electrode ARING and CASE.

To measure cardiac impedance, minute ventilation circuit 22 monitors the voltage differential present between pairs of electrodes as excitation pulses are being injected as described above. Again, the electrodes from which voltage differentials are monitored will vary depending upon whether atrial or ventricular measurements are being made. In one embodiment of the invention, the same electrodes (i.e., VRING and CASE for ventricular, ARING and CASE for atrial) are used for both delivery of excitation pulses and voltage differential monitoring. It is contemplated, however, that the electrode combinations for excitation and measurement may be among the programmable settings which may be altered post-implant with the programming system.

An impedance measurement preamplifier circuit ZMEAS PREAMP 48 is coupled to the voltage differential measurement electrodes during delivery of the excitation pulses. ZMEAS PREAMP circuit 48 comprises three stages. The first is a low-noise a high-pass filtering function. The second stage is a gain amplifier (with a gain of 8 in the presently preferred embodiment). The final stage is a 16-Hz sample-and-hold circuit. As noted above, biphasic excitation pulses are delivered at a rate of 16-Hz; accordingly, sixteen voltage differential measurements are made each second. The sample-and-hold stage of ZMEAS PREAMP circuit 48 holds each of these voltages for presentation to remaining circuitry in minute ventilation circuit 22.

It is believed that the design and implementation of the preamplifier, gain, and sample-and-hold stages of ZMEAS PREAMP circuit 48 would be a matter of routine engineering to those of ordinary skill in the circuit art. Accordingly, the details of the design of ZMEAS PREAMP circuit 48 will not be described herein.

With continued reference to FIG. 2, the 16-Hz sampled output voltages from ZMEAS PREAMP circuit 48 are presented to the minute ventilation low-pass filter circuit MV LPF 47, which as noted above has a passband of 0.05- to 0.8-Hz in the presently preferred embodiment of the invention. Again, it is believed that the design and implementation of MV LPF circuit 47 would be a matter of routine engineering to those of ordinary skill in the art. The output from MV LPF circuit 47 is a voltage waveform whose level at any given time is directly proportional to cardiac impedance measured between the selected electrodes. Thus, the MV LPF output signal will be referred to herein as an impedance waveform.

After bandpass filtering in MV LPF circuit 47, the impedance waveform is provided to a delta modulator circuit DELTAMOD 52, which performs an analog-to-digital conversion (ADC) function. At the beginning of each 16-Hz cycle defined by the ZMEAS PREAMP sample-and-hold operation, DELTAMOD 52 compares the impedance waveform voltage present at the output of MV LPF circuit 47 with the impedance waveform voltage present during the immediately preceding 16-Hz cycle, and determines a Δ value representing the difference between those two voltages.

DELTAMOD circuit 52 defines a "step size" for expressing the Δ values that it computes at the beginning of each 16-Hz cycle. In the presently preferred embodiment of the invention, DELTAMOD 52 defines a step size of 26-mV for ventricular impedance measurement, and a step size of 14-mV for atrial impedance measurement. Thus, for example, if the difference between the ventricular impedance waveform voltage for two successive 16-Hz voltage measurements was 260-mV (i.e., Δ=260-mV), DELTAMOD circuit 52 would express this as a count value of 10 ((Δ/step size)=(260-mV divided by 26-mV)). In this case, DELTAMOD circuit 52 would increment MV REG 49 by ten during the 16-Hz cycle.

DELTAMOD circuit 52 generates a count value, and increments MV REG 49 accordingly, during each 16-Hz cycle defined by the sample-and-hold operation of ZMEAS PREAMP circuit 48 (i.e., every 0.0625 seconds). Thus, over a two-second interval, thirty-two such count values are generated and summed in MV REG 49.

At the conclusion of every two-second interval, the accumulator value in MV REG 49 is provided, via I/O lines 38, to pacing/control circuit 20, and in particular, to CPU 32 for processing in accordance with the rate-response algorithm of the present invention, to be hereinafter described in greater detail. For the purposes of the present disclosure, the value provided to CPU 32 every two-seconds from MV REG 49 will be referred to as an MV COUNT value. When a two-second MV COUNT value is provided to CPU 32, MV REG 49 is reset to zero, in preparation for deriving another MV COUNT value, i.e., accumulating another two seconds' worth of DELTAMOD count values.

ACTIVITY SENSING

As previously noted, pacemaker 10 in accordance with the presently disclosed embodiment of the invention uses both activity sensing and minute ventilation measurement in establishing its variable rate-responsive pacing rate. In the presently preferred embodiment of the invention, activity sensor circuit 21 in pacemaker 10 utilizes a piezoelectric, microphone-like sensor, designated with reference numeral 60 in FIG. 2, for performing activity sensing. Piezoelectric sensor 60 is preferably bonded to the inner surface of the pacemaker's hermetic enclosure, in accordance with conventional practice in the art. Such an arrangement is disclosed, for example, in the above-referenced U.S. Pat. No. 4,485,813 to Anderson et al., assigned to the assignee of the present invention and hereby incorporated by reference herein in its entirety. A similar arrangement is also disclosed in the above-referenced U.S. Pat. No. 5,052,388 to Sivula et al.

As in conventional activity-responsive pacemaker systems such as disclosed in the Sivula et al. '388 and Anderson '813 patents, piezoelectric sensor 60 in pacemaker 10 of the present invention provides a raw electrical signal to an activity signal processing circuit ACT PROC 62 in activity circuit 21, which bandpass filters and processes the activity signal for use in establishing the pacemaker rate. Peaks in the bandpass-filtered activity signal which exceed a predetermined threshold are interpreted by system 62 as an indication of patient activity of sufficient magnitude that an increase in pacing rate may be warranted. The predetermined threshold, which may be among the programmably selectable values of pacemaker 10, is intended to screen out background "noise" in the sensor output signal indicative of low patient activity, or of physical stresses detected by sensor 60 which are not actually indicative of patient activity.

Each occurrence of a peak in the bandpass-filtered sensor signal which exceeds the predetermined threshold is referred to herein as an "ACTIVITY COUNT." A sum of ACTIVITY COUNT values, maintained in an activity register 64 in sensor circuit 21, is computed over a predetermined period of time, e.g., over two second intervals. In accordance with the presently disclosed embodiment of the invention, two-second ACTIVITY COUNT sums are provided, via I/O lines 38, to pacing/control circuit 20, in a manner similar to that for providing minute ventilation accumulator values from MV REG 49 to circuit 20. Then, CPU 32 can use the two-second ACTIVITY COUNT values and minute ventilation values in computing the rate-responsive "sensor rate," as will be hereinafter described in greater detail.

(The concept of deriving, from a piezoelectric element, activity "counts" representative of the level of a patient's physical activity, is well known and understood in the prior art, as exemplified by the above-noted Anderson '813 and Sivula '388 patents, and will thus not be described herein in additional detail. It is believed that those of ordinary skill in the art will be familiar with utilization of a piezoelectric sensor to perform activity sensing in an activity-responsive cardiac pacing and will be readily able to implement such a capability in a manner suitable for the purposes of practicing the present invention.)

RATE-RESPONSE TRANSFER FUNCTION

Fundamental to the basic rate response operation of pacemaker 10 is computing a "Sensor Rate" which is based on the amount of detected physical activity (when pacemaker 10 is programmed to an "activity" rate-response mode), on the amount of minute ventilation (when pacemaker 10 is programmed to a "minute ventilation" rate-response mode), or a blended combination of activity and minute ventilation (when pacemaker 10 is programmed to a "dual" rate-response mode). The Sensor Rate thus derived is expressed as an interval of time in units of cycles of crystal oscillator 28 (clock cycles).

In the presently preferred embodiment, the Sensor Rate value is updated every two seconds, based upon input(s) from the enabled sensor(s), i.e., the two-second accumulated values in MV REG 49 (MV COUNT values) and/or the two-second accumulated ACTIVITY COUNT values from activity register 64. Having described how updated MV COUNT and ACTIVITY COUNT values are provided to pacing/control circuit 20 at the end of every two-second interval of pacemaker operation, the manner in which a Sensor Rate value is derived from those values can now be described.

As will be appreciated by those of ordinary skill in the art, the computation of a Sensor Rate value based upon the MV COUNT and ACTIVITY COUNT values supplied from minute ventilation circuit 22 and activity circuit 21, respectively, involves numerous computations performed primarily by CPU 32 on variable and programmable values which are maintained in memory unit 30 of pace/control circuit 20.

Table 1 sets forth various definitions, acronyms, and abbreviations that are used in the following description of Sensor Rate determination in accordance with the presently disclosed embodiment of the invention.

TABLE 1

| NAME/ACRONYM | DESCRIPTION |
|---|---|
| ACTIVITY COUNT | The output from Activity Circuit 21, counts of activity sensor signal peaks above a predetermined threshold per two seconds. Range is 0 to 24. |
| MV COUNT | The output from Minute Ventilation circuit 22, counts from delta modulator DELTAMOD 52, reflecting changes in amplitude and frequency of transthoracic impedance per two seconds. Range is 0 to 511. |
| DMV | Delta MV, the difference between LSTA and LTA (see below). |

TABLE 1-continued

| NAME/ACRONYM | DESCRIPTION |
|---|---|
| Limited Short-Term Average (LSTA) | A weighted average of MV COUNT values, in units of counts per two seconds, with the weighting or emphasis being placed on the latest 32 seconds. This average is not allowed to increase beyond the value at which the Target Rate would be greater than the Upper Sensor Rate. |
| Long-Term Average (LTA) | A weighted average of MV COUNT values, in units of counts per two seconds, with the weighting or emphasis being placed on the latest several hours. |
| Minute Ventilation (MV) | The product of respiration rate and tidal volume, a physiologic indicator of metabolic demand. Variations in transthoracic impedance are proportional to minute ventilation variations. |
| Sensor3Counts | The combined or "blended" sensor input per two seconds. The range is 0 to 255. |
| Sensor Counts | Sensor3Counts if both minute ventilation sensing and activity sensing are activated; MV COUNTS if only minute ventilation sensing is activated; ACTIVITY COUNTS if only activity sensing is activated |

Table 2 sets forth various programmable parameters of pacemaker 10 which are utilized in connection with its rate-responsive operation.

TABLE 2

| PARAMETER NAME | DESCRIPTION |
|---|---|
| Sensor | Sensor(s) upon which rate-response operation is based (programmable to "DUAL," "ACTIVITY," or "MINUTE VENTILATION." |
| LowerSensorRate | Lowest pacing rate allowed for patient (programmable to 30 to 180 beats per minute (BPM)) |
| UpperSensorRate | Maximum value that sensor rates can achieve (programmable to 80 to 180 BPM) |
| UpperSensorRateInterval | UpperSensorRate expressed in units of cycles of clock 28 in pace/control unit 20 |
| ADLRate | Desired rate to achieve during daily activities ("Activities of Daily Living") (programmable to 40 to 180 BPM) |
| ADLRateinterval | ADLRate expressed in units of cycles of clock 28 in pace/control unit 20 |
| URCounts | Least Sensor3Counts value that is mapped to UpperSensorRate (i.e., the minimum Sensor3Counts value that can cause pacing at the UpperSensorRate) (programmable to 15 to 255) |
| ADLCounts | Least Sensor3Counts mapped to ADLRate (i.e., the minimum Sensor3Counts value that can cause pacing at the ADLRate) (programmable to 5 to 250) |
| ADLWidth | Number of Sensor3Counts mapped to ADLRate (i.e., the width of a range of Sensor3Counts values that will cause pacing at the ADLRate) (programmable to 0, 3, 6, 1 2, and 25% of URCounts) |
| ScalingFactor | Value by which ACTIVITY COUNT values are multiplied to put them on the same scale as MV COUNT values (programmable to 0 to 40) |
| MVSlewRateLimit | Fraction of URCounts that MV COUNT values are allowed to change in any given two-second interval (programmable to 1.5, 3, 6, 12, 25, 50, or 100% of URCounts, or OFF) |
| MVHighCheck | Set if MVHigh Intervention operation is enabled. |
| ActivityCrossCheckLevel | Fraction of ADLCounts considered low for activity cross check (programmable to 0, 12, 25, 37, 50, 62, 75, 87, or 100% of ADLCounts) |
| MVSwitchLevel | Fraction of ADLCounts at which normal MV processing resumes following MV High intervention (programmable to 0, 25, 50, 75, or 100% of ADLCounts) |
| URTimeCriteria | Amount of two-second intervals considered too long at UR (i.e., the minimum length of time considered to be too long for continuous pacing at the programmed UpperSensorRate) (programmable to 0, 4, 8, . . . , 28 minutes) |
| HighRatecrossCheck | Set if high rate cross check operation is enabled |
| MVCrossCheckLimit | Fraction of the value (URCounts - ADLCounts - ADLWidthCounts) that Sensor3Counts cannot exceed |

TABLE 2-continued

| PARAMETER NAME | DESCRIPTION |
| --- | --- |
|  | without corroboration in DUAL sensor mode (programmable to 0, 1 2.5, 25, 50, or 1 00% of the value (URCounts - ADLCounts - ADLWidthCounts) above the value (ADLCounts + ADLWidth) |
| MVSensorStatus | Status of the minute ventilation sensor (programmable to "ON," "OFF," or "SUSPEND"). |
| MVChamber | Chamber (ventricular or atrial) in which MV sensing is to occur |
| CIntercept1 | Interval intercept for the COMBINE function segment whose other endpoint is LowerRateinterval |
| CIntercept2 | Interval intercept for the COMBINE function segment whose other endpoint is CIntercept1 |
| CSlope1 | Slope of the COMBINE function segment from CIntercept1 to LowerRateInterval |
| CSlope2 | Slope of the COMBINE function segment from CIntercept2 to CIntercept1 |
| Acceleration | Constant which defines how aggressively the SensorRate increases toward the TargetRate (programmable to 15, 30, or 60 seconds) |
| Deceleration | Constant which defines how aggressively the SensorRate decreases toward the TargetRate (programmable to 2.5, 5, or 10 minutes, (or "Exercise" if Sensor is set to "ACTIVITY") |
| MaxWork | Amount of work which results in full use of work deceleration (programmable to (54 × rate range). Applicable to "ACTIVITY" only mode with work-modulated pacing rate decay |
| WorkDecrement | Amount by which work is decremented every two seconds when TargetRate is less than current rate or TargetRate is below RestRate (programmable to MaxWork/600). Applicable to "ACTIVITY" only mode with work-modulated pacing rate decay |
| SwitchRateInterval | Point at which work deceleration takes effect, if work is greater than 0 (programmable to 0.8 of rate range). Applicable to "ACTIVITY" only mode with work-modulated pacing rate decay |
| RestRate | Rate which defines when the patient is at rest. Work is incremented when target rate is at or above RestRate and decremented otherwise. Applicable to "ACTIVITY" only mode with work-modulated pacing rate decay |

Figure 4:
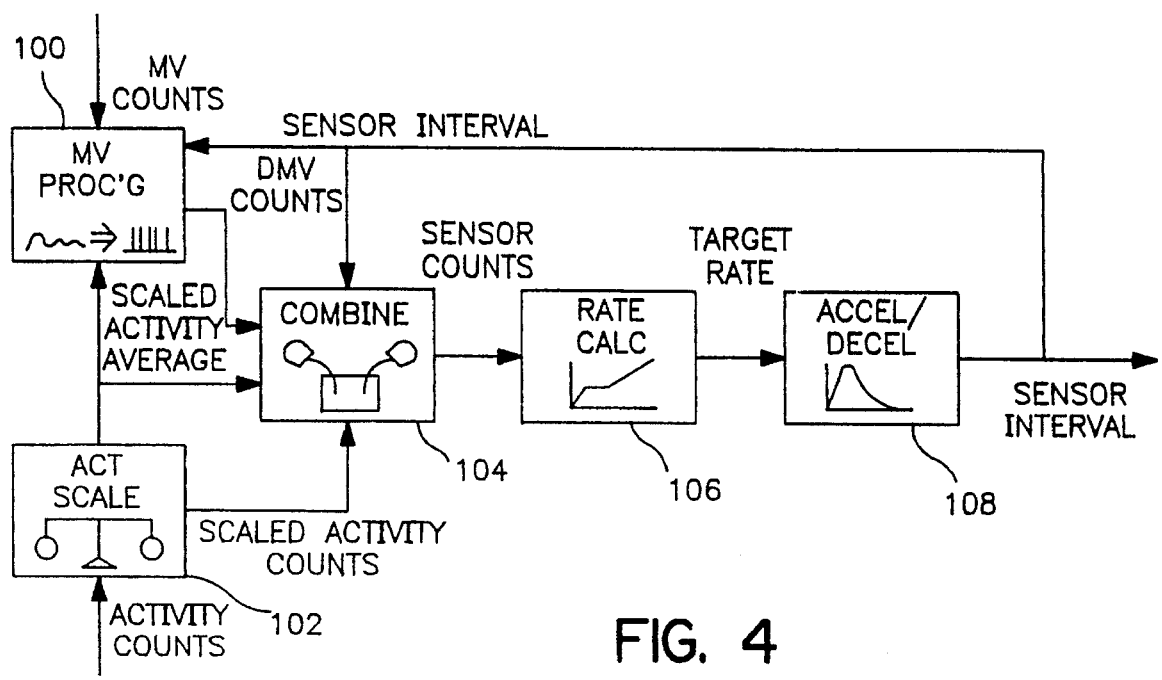
FIG. 4 is a functional block diagram representing the operation of the pacemaker of FIG. 2 in a rate-response mode.

The overall algorithm for determining a Sensor Rate value based upon minute ventilation and activity sensing in pacemaker 10 in accordance with the presently disclosed embodiment of the invention is generally illustrated in the functional block diagram of FIG. 4. Each block in FIG. 4 represents one stage in the Sensor Rate determination process. As will be hereinafter described in greater detail, many of the stages represented in FIG. 4 are performed by CPU 32 in pace/control circuit 20 (see FIG. 2). For example, the block MV PROC'G identified with reference numeral 100 in FIG. 4 corresponds to a stage of numerical processing of MV COUNT values provided every two seconds, this numeral processing being performed by CPU 32 under control of programming instructions stored in memory unit 30. Likewise, other stages represented in FIG. 4, e.g., COMBINE stage 104, RATE CALC stage 106, etc. . . . , involve mainly numerical processing performed by CPU 32.

Figure 5:
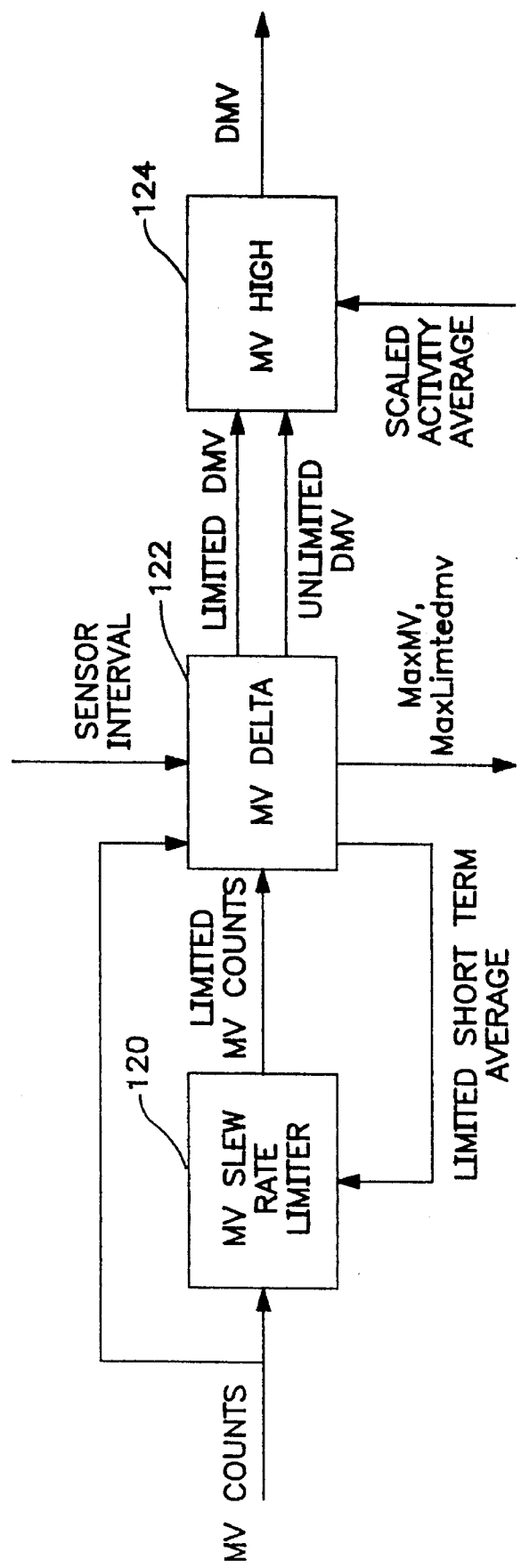
FIG. 5 is a further functional block diagram representing minute ventilation operation of the pacemaker of FIG. 2 in the rate-response mode.

In the case of MV PROC'G stage 100 of the Sensor Rate determination algorithm, three sub-stages are involved, as illustrated in the functional block diagram of FIG. 5. The first step in the MV PROC'G stage, represented by block 120 in FIG. 5, is to perform a slew rate limiting function on the MV COUNT values provided from minute ventilation circuit 22 every two seconds. The limiting function of block 120, which results in the computation of a value "LimitedMVCounts," is performed according to the following equation:

LimitedMVCounts=MIN{MVCOUNT,INT{LSTA+SlewRateLimit-Counts×2}} where MV COUNT is the most recent "two-second" MV COUNT value provided from minute ventilation circuit 22, LSTA is a Limited Short-Term Average value of MV COUNT values, (to be hereinafter described in .greater detail), and where SlewRateLimitCounts is defined as in the following equation:

$$\text{SlewRateLimitCounts} = INT\left(URCounts \times \frac{\text{SlewRateLimit}}{100}\right)$$

with URCounts and SlewRateLimit being programmable constant values, and with INT and MIN being the well-known integer and minimum mathematical functions, respectively. In the presently preferred embodiment of the invention, URCounts reflects the smallest MV COUNT value which can result in a maximum Sensor Rate value, and is programmable from 0 to 255. SlewRateLimit represents a limit on the maximum allowable positive difference between MV COUNT/2 and LSTA, and is expressed as a fraction of URCounts value. In the presently preferred embodiment of the invention, SlewRateLimit is programmable to 1.5, 3, 6, 12, 25, 50, or 100% of URCounts, or OFF.

After computing the LimitedMVCounts value as set forth in the above equation, the next step in the block diagram of FIG. 5, represented by MV Delta block 122, involves using the LimitedMVCounts value in the computation and/or updating of other values, including Limited DMV, Unlimited DMV, LSTA, and MaxMV values.

An LTA (Long-Term Average) value is recursively computed in block 122 according to the following equation:

$$LTA = LTA + INT\left(\frac{\left(\frac{\text{Limited}MV\text{Counts}}{2}\right) - LTA}{\text{LongTermTime}}\right)$$

where LongTermTime is, in the presently preferred embodiment, approximately hours (expressed in the foregoing equation as 32,768 two-second intervals).

The Limited Short-Term Average (LSTA) value is computed according to the following equation:

where ShortTermTime is, in the presently preferred embodiment is 32 seconds (expressed in the above equation as 16 two-second intervals).

$$LSTA = \text{MIN}\left(LSTA + INT\frac{\left(\frac{(\text{Limited}MV\text{Counts})}{2}\right) - LSTA}{\text{ShortTermTime}}, LTA + UR\text{Counts}\right)$$

An USTA (Unlimited Short-Term Average) value is computed according to the following equation:

$$USTA = USTA + INT\left(\frac{\left(\frac{MV\text{Counts}}{2}\right) - USTA}{\text{ShortTermTime}}\right)$$

A LimitedDMV value, representing the difference between the LSTA and LTA values is defined as follows:

LimitedDMV=MAX(0,INT(LSTA-LTA))

An UnlimitedDMV value is computed in block 122 according to the following equation:

UnlimitedDMV=INT(USTA-LTA)

Finally, a MaxLimitedMV value is computed in block 122 according to the following equation:

MaxLimitedMV=MAX(LimitedDMV, MaxLimitedMV)

After performing the above-described processing substeps in MV Delta block 122 of FIG. 5, the next step of the Sensor Rate computation process is represented by MV High block 124 in FIG. 5. The MV High processing occurs as a safeguard against undesirable high-rate pacing for prolonged periods of time. If minute ventilation sensing is continuously high for a predetermined period of time (a programmable value designated as UR Time Criteria, programmable to 0, 4, 8, . . . 28 minutes) and activity sensing circuitry 21 does not corroborate a heightened physiologic need (to be hereinafter described) during the same time period, so-called MV High Intervention occurs.

In accordance with the presently preferred embodiment of the invention, minute ventilation sensing is considered too high if the UnlimitedDMV value computed as described in the equation above is greater than URCounts. On the other hand, activity sensing is considered to be too low if a ScaledActivityAverage value (the definition of which to be hereinafter described in further detail) is less than a predetermined (programmable) ActivityCrossCheckCounts value, which is defined according to the following equation:

$$\text{ActivityCrossCheckCounts} = INT\left(\frac{\text{ActivityCrossCheckLevel} \times ADL\text{Counts}}{100}\right)$$

where ActivityCrossCheckLevel reflects an ACTIVITY COUNT level which is considered to be low for a given patient, and where ADLCounts ("Activities of Daily Living" counts) is a programmable value corresponding to the least number of SensorCounts which can cause pacing at the rate deemed to be appropriate for a patient's daily activities. ActivityCrossCheckLevel is preferably expressed as a fraction of ADLCounts (e.g., 0%, 12.5%, 25%, 37.5%, 50%, 62.5%, 75%, 87.5%, 100%). In the presently disclosed embodiment of the invention, a so-called ADLRate is programmably determined (between 40 and 180 paces per minute), where ADLRate is the pacing rate deemed by the implanting physician to be appropriate for a given patient's daily activities. ADLCounts, in turn, defines the least value for SensorCounts which can cause pacemaker 10 to pace at the ADLRate. In one embodiment, ADLCounts is expressed in terms of a percentage of URCounts, where URCounts is the least value for SensorCounts which can cause pacemaker 10 to pace at its programmed UpperSensorRate (i.e., the maximum pacing rate of pacemaker 10 when pacing in MV and/or Activity Sensing mode). (The functions and parameters of pacemaker 10 relevant to the ADL ("Activities of Daily Living") feature thereof will be described hereinbelow in further detail.)

If, according to the above-noted criteria for considering MV COUNTs high and ACTIVITY COUNTs low, minute ventilation is considered too high and sensed activity too low, CPU 32 increments a variable designate MVHighTime; otherwise, MVHighTime is reset to zero. If the MVHighTime variable reaches the value URTimeCriteria (defined as noted above) MVHigh Intervention occurs. During MVHigh Intervention, DMV is set to a predetermined (programmable) value MVSwitchCounts, which is defined according to the following equation:

$$MV\text{SwitchCounts} = INT\left(\frac{MV\text{ Switch Level} \times ADL\text{ Counts}}{100}\right)$$

MVSwitchLevel is a programmable value representing a fraction of ADLCounts at which normal minute ventilation processing resumes following an episode of MVHigh Intervention. MVSwitchLevel is preferably expressed as a fraction of ADLCounts (e.g., 0, 25, 50, 75, or 100% of ADLCounts).

During MVHigh Intervention, LimitedDMV as calculated above is monitored until it is at or below MVSwitchCounts calculated according to the above equation, at which time MVHigh Intervention ends and DMV is reset to LimitedDMV.

As noted above, ACTIVITY COUNT values are collected every two seconds from Activity Register 64. Each time a new ACTIVITY COUNT value is provided to pace/control circuit 20, the previous ACTIVITY COUNT value is maintained in a register in order that a four-second activity count (4SecActCounts) value can be computed. Specifically, 4SecActCounts is given by the following equation:

4SecActCounts=ACTIVITYCOUNT+LastActCounts where ACTIVITY COUNT is the value obtained from Activity Register 64 in activity sensor circuit 21 at the end of a current two-second interval, and where LastActCounts is the ACTIVITY COUNT value obtained from register 64 at the end of the preceding two-second interval.

The 4SecActCounts value is then scaled to the range of the minute ventilation sensing circuitry 21 to produce a ScaledActivityCounts value. This scaling operation occurs in block 102 of FIG. 4, and results in derivation of a scaled activity counts value SActCnt. SActCnt is derived according to the following equation:

$$SActCnt = INT\left(\frac{4SecActCounts \times ScalingFactor}{2}\right)$$

A ceiling value of 255 is imposed on the SActCnt value; that is, if the SActCnt value computed according to the equation above is greater than 255, SActCnt is set to 255.

derived. First, the value of SActCnt is set to the smaller of SActCnt and URCounts; that is, the SActCnt value derived in accordance with the equation above is reset according to the following equation:

$$SActCnt = MIN(URCounts, SActCnt)$$

Then, the blended sensor value Sensor3Counts is computed according to the following equation:

$$Sensor3Counts = \begin{cases} DMV, & DMV \geq SActCnt \\ INT\left(\frac{(SActCnt \times C(CurrentInterval) + DMV \times (128 - C(CurrentInterval)))}{128}\right), & \text{otherwise} \end{cases}$$

where the C function is given according to the following equation:

$$C(CurrentInterval) = \begin{cases} 128, & CurrentInterval \geq LowerRateInterval \\ INT\left(\frac{CSlope1 \times (CurrentInterval - C1)}{256}\right) + 96, & C1 \leq CurrentInterval < LowerRateInt \\ INT\left(\frac{CSlope2 \times (CurrentInterval - C2)}{256}\right), & C2 < CurrentInterval < C1 \\ 0, & CurrentInterval \leq C2 \end{cases}$$

As noted above, an average of the scaled activity counts value SActCounts is maintained for use in MVHigh Intervention and High Rate Cross Check operation. This average, designated SActAverage, is computed according to the following equation:

$$SActAverage = SActAverage + \frac{SActCnt - SActAverage}{8}$$

Also, a maximum scaled activity average value, MaxSActAverage, is maintained by CPU 32 for activity scaling, to be described hereinbelow in further detail. MaxSActAverage is computed according to the following equation:

$$MaxSActAverage = MAX(INT(SActAverage), MaxSActAverage)$$

In accordance with one aspect of the present invention, if both activity and minute ventilation sensing are enabled in pacemaker 10, a "blending" function is performed on the sensor outputs. This blending function is structured so that activity sensing has influence on the SensorRate in the range from the programmed LowerSensorRate up to the "Activities of Daily Living" (ADL) rate, which, as noted above, is programmable by the physician to a rate which is deemed appropriate for the patient's normal daily activity level. At rest, activity sensing dominates in the computation of SensorRate. As SensorRate increases, minute ventilation sensing gains greater influence, so that above the ADL rate, minute ventilation is dominant. The "blending" of activity sensor output and minute ventilation sensor output occurs in COMBINE block 104 of FIG. 4. As shown in FIG. 4, the DMV value derived as previously described with reference to FIG. 5, and the SActCnt value derived from the activity sensor are provided as inputs to the COMBINE stage 104 of the SensorRate computation algorithm. In COMBINE stage 104, a blended sensor counts value Sensor3Counts is where the values of C1, C2, CSlope1, and CSlope2, respectively, will vary depending upon the relationship between UpperSensorRate and ADLRate, and between ADLRate and LowerSensorRate. In particular, if UpperSensorRate≥ADLRate+10, and if ADLRate>LowerSensorRate+10, then C1, C2, CSlope1 and CSlope2 are given by the following equations:

$$C1 = Interval(ADLRate - 10)$$
$$C2 = Interval(ADLRate + 10)$$

$$CSlope1 = \frac{32 \times 256}{LowerRateInterval - C1}$$

$$CSlope2 = \frac{96 \times 256}{C1 - C2}$$

(In the foregoing and other equations herein, the "interval" function is given by Interval(x)=7680/x, representing a conversion from a rate value to an interval value, in unites of clock cycles.)

However, if UpperSensorRate≤ADLRate+10 and ADLRate≥LowerSensorRate+10, then C1, C2, CSlope 1 and CSlope2 are given by the following equations:

$$C1 = LowerRateInterval$$
$$C2 = Interval(ADLRate + 10)$$
$$CSlope1 = 0$$

$$CSlope2 = \frac{128 \times 256}{C1 - C2}$$

On the other hand, if UpperSensorRate<ADLRate+10, and ADLRate>LowerSensorRate+10, then C1, C2, CSlope1 and CSlope2 are given by the following equations:

$$C1 = Interval(ADLRate - 10)$$

-continued $C2 = \text{UpperSensorRateInterval}$ $$CSlope1 = \frac{32 \times 256}{\text{LowerRateInterval} - C1}$$

$$CSlope2 = \frac{96 \times 256}{C1 - C2}$$

Finally, if UpperSensorRate<ADLRate+10 and ADLRate≦LowerSensorRate+10, then C1, C2, CSlope1 and CSlope2 are given by the following equations:

$C1 = \text{LowerRateInterval}$
$C2 = \text{UpperSensorRateInterval}$
$CSlope1 = 0$ $$CSlope2 = \frac{128 \times 256}{C1 - C2}$$

In addition to computing a Sensor3Coums value in accordance with the foregoing equations, another operation performed in connection with COMBINE stage 104 of the Sensor Rate computation algorithm is a high rate cross check which involves a comparison of the ScaledActivityAverage value computed in accordance with the equation above with the ActivityCrossCheckCounts value discussed in conjunction with the equation above. If ScaledActivityAverage is less than Activity CrossCheckCounts and DMV is greater than MVCrossCheckCounts, Sensor3Counts is set to MVCrossCheckCounts, where MVCrossCheckCounts is given by the following equation:

$$\text{MVCrossCheckCounts} = \text{ADLWidthCounts} + \text{TempOffset}$$

where TempOffset is given by:

$$\text{TempOffset} = \left( INT \left( \frac{\text{URCounts} - \text{ADLCounts} - (\text{ADLWidthCounts} \times \text{MVCrossCheckLimit})}{100} \right) + \text{ADLCounts} \right)$$

Where MVCrossCheckLimit is expressed as a fraction of (URCounts—ADLCounts—ADLWidthCounts), e.g., 0%, 12.5%, 25%, 50%, or 100%.

If the HighRateCrossCheck does not limit DMV, the combine function described above with reference to the equations for SActCnt, Sensor3Counts, etc. . . . , is used. The combine function is structured so that Activity input has influence from LowerSensorRate to ADLRate. At rest, activity is favored in the combine function. As the SensorRate increases, minute ventilation has greater influence so that above ADLRate, Sensor3Counts=DMV. At all times, if DMV is greater than SActCnt, DMV is used.

The next stage of SensorRate computation as depicted in FIG. 4 is the RATE CALC stage 106, which constructs a rate response curve from the programmed UpperSensorRate, the programmed ADLRate, the programmed LowerRate, the ADLCounts and URCounts values, and the ADLWidthCounts value.

To compute the TargetRate, two slope values, RSlope1 and RSlope2, and an DLWidthCounts value, are computed, according to the following equations:

$$RSlope1 = \frac{\text{ADLRate} - \text{LowerSensorRate}}{\text{ADLCounts}} \times 256$$

-continued $$RSlope2 = \frac{\text{UpperSensorRate} - \text{ADLRate}}{\text{URCounts} - \text{ADLCounts} - \text{ADLWidthCounts}} \times 256$$

$$\text{ADLWidthCounts} = INT \left( \frac{\text{URCounts} \times \text{ADLWidth}}{100} \right)$$

Then, a TargetRate value is computed according to the following equation:

$$\text{TargetRate} = \begin{cases} INT \left( \frac{\text{RSlope1} \times \text{SensorCounts}}{256} \right) + \\ \text{LowerSensorRate}, \\ \text{SensorCounts} < \text{ADLCounts} \\ \text{ADLRate}, \text{ADLCounts} \leq \\ \text{SensorCounts} \leq \text{ADLCounts} + \text{ADLWidthCounts} \\ INT \left( \frac{\text{RSlope2} \times \text{SensorCounts}}{256} \right) + \\ \text{ADLRate}, \text{ADLCounts} \\ \text{ADLWidthCounts} < \text{SensorCounts} < \text{URCount} \\ \text{UpperSensorRate}, \text{SensorCounts} \geq \text{URCounts} \end{cases}$$

where the value SensorCounts is Sensor3Counts, as computed in accordance with the equation above, if both minute ventilation and activity sensing are enabled. If one sensor is not enabled, SensorCounts in the above equation is the count value from the enabled sensor (i.e. , SensorCounts=DMV if only minute ventilation sensing is enabled, and SensorCounts=SActCnt if only activity sensing is enabled).

The TargetRate value is then convened to a TargetInterval value as follows:

$$\text{TargetInterval} = INT \left( \frac{\left( INT \left( \frac{15360}{\text{TargetRate}} \right) + 1 \right)}{2} \right)$$

This concludes the RATE CALC stage 106 of the algorithm represented in FIG. 4. The next stage, SMOOTH block 108, involves computation of a SensorInterval, which can differ from the TargetInterval in that acceleration and deceleration parameters can have an effect upon how quickly the actual pacing rate (interval) of pacemaker 10 can approach the Target Rate (Interval). That is, the SensorInterval is prevented from increasing or decreasing too quickly (in order to more closely mimic natural cardiac response) in spite of the potential for very rapid changes in the TargetRate (Interval) based upon minute ventilation and activity sensing inputs.

In accordance with the preferred embodiment, if the TargetInterval computed according to the equation above is less than or equal to the current SensorInterval, then the SensorInterval is decreased so that the pacing rate accelerates towards the TargetRate. A programmable Acceleration parameter is used to control how quickly the pacing rate increases towards the TargetRate. During acceleration, pacemaker 10 calculates a new SensorInterval (every two seconds) as follows:

SensorInterval = SensorInterval +

$$\left( \left( \frac{(\text{TargetInterval} - \text{SensorInterval})}{\text{Acceleration}} \right) \text{OR'edwith4} \right)$$

On the other hand, if the TargetInterval is greater than the SensorInterval, then the SensorInterval is increased so that the pacing rate decelerates towards the TargetRate. A programmable Deceleration parameter is used to control how quickly the pacing rate decreases toward the TargetRate. During deceleration, pacemaker 10 computes a new SensorInterval (every two seconds) as follows:

SensorInterval = SensorInterval +

$$\left( \left( \frac{(\text{TargetInterval} - \text{SensorInterval})}{\text{Deceleration}} \right) \text{OR'edwith4} \right)$$

In the above equations for SensorInterval, the OR'ing with 4 ensures that the SensorInterval is always increased or decreased by at least an amount of time corresponding to $4/256$ of a cycle of clock 28 (see FIG. 1).

In either acceleration or deceleration, the SensorInterval is not allowed to exceed the programmed LowerRateInterval or fall below the programmed UpperSensorRateInterval.

In the presently preferred embodiment, an Acceleration constant corresponding to 30-Sec and a Deceleration constant corresponding to 2.5-Min is considered suitable, although as noted above, the Acceleration and Deceleration parameters may be among those that are programmable by the implanting physician. In addition, it is contemplated that the present invention may be advantageously practiced in conjunction with a more robust acceleration/deceleration algorithm, such as the one described in detail in U.S. Pat. No. 5,312,453 to Shelton et al., entitled "Rate Responsive Cardiac Pacemaker and Method for Work Modulating Pacing Rate Deceleration." The Shelton et al. '453 patent is commonly assigned to the assignee of the present invention and is hereby incorporated by reference herein in its entirety.

Figure 6:
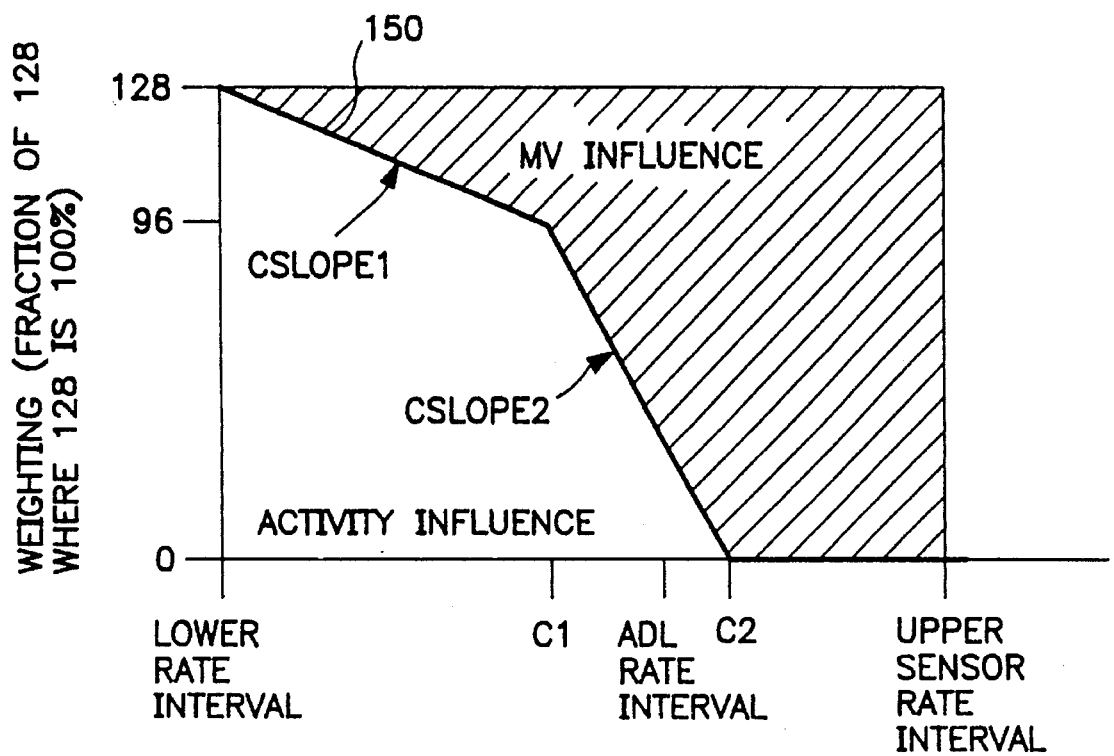
FIG. 6 is a graphical representation of the sensor blending function of the pacemaker from FIG. 2 operating in a rate-response mode.
Figure 7:
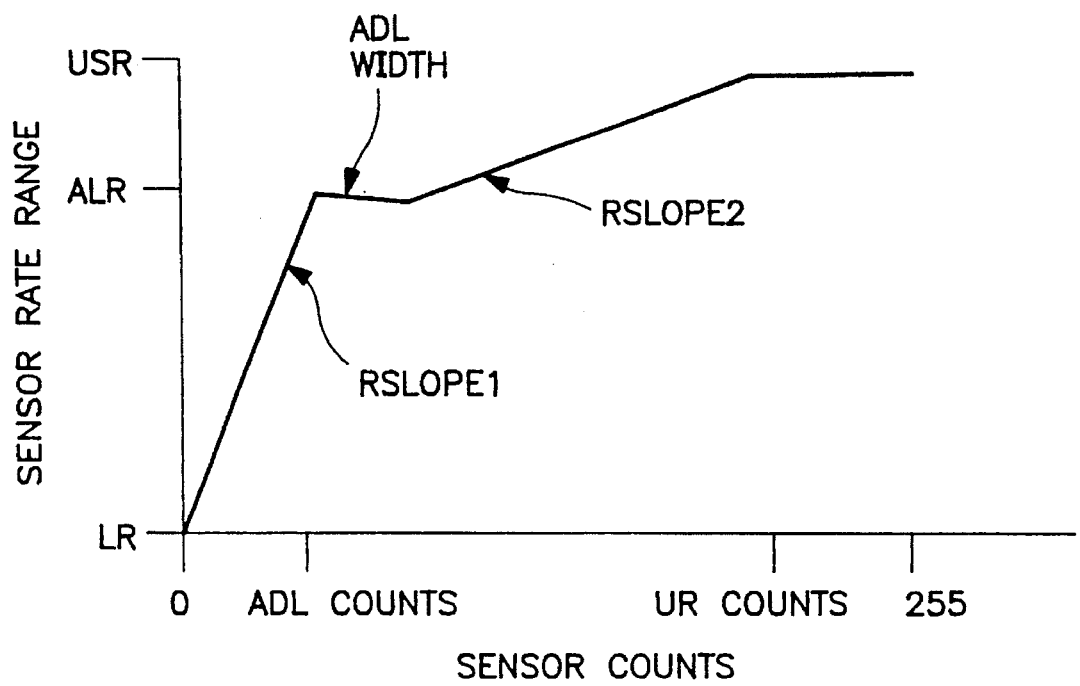
FIG. 7 is a graphical representation of the rate-transfer function of the pacemaker from FIG. 2 operating in a rate-response mode.

Turning now to FIGS. 6 and 7, there are shown alternative graphical representations of the rate response transfer function for pacemaker 10 which results from the computations based on minute ventilation and activity sensing as set forth above with reference to FIGS. 1–5 and the foregoing equations.

In the graph of Sensor Interval Range in FIG. 6, the horizontal axis represents Sensor Interval, expressed in units of cycles of clock 28 (see FIG. 1). As shown in FIG. 6, the Sensor Interval ranges between the programmed Lower Rate Interval (e.g., the inverse of the programmed UpperRate-Limit or URL) to the UpperSensorRateInterval, the maximum interval between pacing pulses allowable for pacemaker 10 (i.e., the inverse of the programmed UpperRateLimit or URL).

The vertical axis in FIG. 6 represents the weighting of minute ventilation contribution and activity contribution to the calculated SensorRate. The lowest point on the vertical axis represents a zero percent contribution to the calculated SensorRate (i.e., where either sensed activity or sensed minute ventilation has no effect upon the calculated SensorRate), while the highest point on the vertical axis represents a 100% contribution.

The rate response transfer function which results from the calculations described above with reference to the foregoing equations is represented in FIG. 6 by plot line 150. Specifically, the influence of sensed minute ventilation is represented by the shaded area above plot line 150, while the influence of sensed activity is represented by the area below plot line 150. FIG. 6 shows that minute ventilation will always prevail activity sensing in the rate response transfer function when DMV is greater than SActCnts. Thus, when pacemaker 10 is pacing at the programmed Lower Rate Interval (i.e., at the programmed URL), the output of the blending function will depend entirely upon sensed patient ACTIVITY COUNTs.

Expressed in an alternative manner, at the LowerRateInterval, the ACTIVITY COUNT value is multiplied by a weighting factor of 100, while the MV COUNT value is multiplied by a weighting factor of 0. This weighting factor determines the influence or dominance of the ACTIVITY COUNT and MV COUNT values in the determination of a SensorRate. As would be appreciated by those of ordinary skill in the art, a weighting factor of zero for one count value would imply that the count value has no influence in the rate calculation, and that the SensorRate determined in accordance with the present invention would depend entirely upon the count value having a weighting factor greater than zero.

With continued reference to FIG. 6, plot line 150 has a downward slope CSlope1 in the sensor interval range between the programmed LowerRateInterval and a point C1 in the sensor interval range, and has a second downward slope CSlope2 in the sensor interval range between point C1 and a second point C2 in the sensor interval range. (The points C1 and C2 are determined based upon the calculations described with reference to the equations above.) Thus, between the LowerRateInterval and point C1 in the graph of FIG. 6, the weighting factor for ACTIVITY COUNT values decreases from 100 at a rate corresponding to CSlope1 as pacing rate increases, and the weighting factor for MV COUNT values increases from 0 at a rate corresponding to CSlope1 as pacing rate increases As shown in FIG. 6, the influence that sensed minute ventilation has upon the calculated SensorInterval increases gradually from zero to approximately 25% between the LowerRateInterval and point C1 in the sensor interval range, the rate of increase in its influence being determined by CSlope1, defined as above. Between points C1 and C2 in the sensor interval range, the influence of sensed minute ventilation on the calculated SensodnInterval increases more rapidly (and conversely, the influence of sensed activity decreases more rapidly), as determined by CSlope2 defined above. Finally, between point C2 and the programmed UpperSensorRateInterval, the calculated SensorInterval depends entirely upon sensed minute ventilation. That is, in the range between C2 and the programmed UpperSensorRateInterval, sensed patient activity has no effect upon the SensorInterval value—the weighting factor for ACTIVITY COUNT values in the rate-response transfer function is zero, while the weighting factor for MV COUNT values in the rate-response transfer function is 100.

In FIG. 7, the rate response transfer function of pacemaker 10 resulting from operation in accordance with the foregoing equations is depicted in an alternative manner, with the variable SensorCounts, computed in accordance with the equation above being plotted along the horizontal axis, and with the SensorRateRange (rather than the SensorIntervalRange as in FIG. 6) being depicted along the vertical axis. As shown in FIG. 7, the SensorRate range extends between the programmed LowerRateLimit (LRL) and the programmed UpperSensorRate (USR), while the SensorCounts variable ranges between 0 and 255, as noted above.

FIG. 7 shows that when SensorCounts is in the range between 0 and ADLCounts, the SensorRate increases at a first slope, RSlope1 computed in accordance with the above equation. When SensorCounts is in the range between ADLCounts and ADLCounts+ADLWidth, the Sensor Rate is level at ADLRate. For SensorCounts between ADLCounts+ADLWidth and URCounts, the SensorRate increases at a second slope, RSlope2 computed in accordance with the above equation. Finally, for SensorCounts between URCounts and 255, the SensorRate is level at the programmed UpperSensorRate.

As described above, the SensorRate determination algorithm employed by pacemaker 10 in accordance with the presently disclosed embodiment of the invention requires several numerical values to be maintained and periodically updated in order to achieve the rate response function as depicted in FIGS. 6 and 7. Among these values are the activity threshold value (which determines what degree of physical activity is deemed to be indicative of patient activity sufficient to increase metabolic demand), and the LSTA (LimitedShortTermAverage) and LTA (LongTermAverage) values associated with minute ventilation detection. In the presently preferred embodiment of the invention, the ActivityThreshold parameter can be programmed to one of five settings: Low, Medium Low, Medium, Medium High, and High.

Some of these values that must be maintained by pacemaker 10, such as activity threshold, will vary from patient-to-patient while others, such as the LSTA and LTA, reflect the unique physiological behavior of a patient over a predetermined period of time (e.g., several hours in the case of the LTA). As a result, it is necessary for these values to be initialized to personalized levels appropriate for the patient prior to pacemaker 10 being operated in the rate-responsive mode. To this end, pacemaker 10 in accordance with the presently disclosed embodiment of the invention is provided with an automatic initialization capability.

In one embodiment of the invention, pacemaker 10 is further provided with an automatic implant detection capability, which enables pacemaker 10 to automatically activate itself into operation with default operating settings and parameters immediately upon implant. With this capability, the automatic initialization of rate-response values to be described hereinbelow can itself be automatically initiated upon implant. One application of this capability is described in detail in co-pending U.S. patent application on the same date as the present application, entitled "Automatic Lead Recognition for an Implantable Medical Device," filed in the name of Wahlstrand et al. and commonly assigned to the assignee of the present invention. The Wahlstrand et al. application is hereby incorporated by reference herein in its entirety.

For an alternative embodiment of pacemaker 10 which does not possess an automatic implant detection capability, pacemaker 10 can be "notified" of implant via a simple downlink telemetry command, the receipt of which causing pacemaker 10 to initiate the automatic initialization procedure.

In either case, in accordance with the presently disclosed embodiment of the invention, automatic initialization of settings related to the rate-response operation of pacemaker 10 is preferably performed within several (e.g., six) hours of implant. Automatic initialization of values related to the "Activities of Daily Living" (ADL) operation of pacemaker 10 is preferably accomplished within several (e.g., ten) days after implant.

The following paragraphs outline how each of the values associated with rate-response operation of pacemaker 10 is initialized at the time of implant:

ActivityThreshold Autoinitialization

Once implant is confirmed (either automatically or through physician programming, as noted above), pace/ control circuit cycles through each activity threshold setting, collecting two-second activity counts to add to a running total associated with each activity setting (i.e., Low, Medium Low, Medium, Medium High, and High. In the presently preferred embodiment, this is done for six hours. After six hours of collecting two-second activity counts, an activity threshold setting is selected. In the presently preferred embodiment of the invention, if the number of activity counts collected at the Medium Low activity threshold setting corresponds to an average input frequency of less than approximately $\frac{1}{16}$-Hz (i.e., less than sixteen activity counts per second), Medium Low is selected as the initial activity threshold setting. Otherwise, a setting of Medium Low, Medium, or Medium High is chosen as follows: If the number of counts collected at the Medium Low setting is less than three times the number of counts collected at the High setting, Medium Low is selected. If not, if the number of counts collected at the Medium setting is less than three times the number of counts selected at the High setting, Medium is selected. Otherwise, Medium High is selected.

LSTA and LTA Autoinitialization

Once implant is confirmed, LTA is initially set to MVCounts. Then, at each two-second interval, it is recalculated using the LTA calculation equations with increasing values of the LongTermTime parameter. Preferably, LongTermTime increases exponentially (i.e., 1, 2, 4, 8, etc. . . . ) until it reaches its final value of 32,768.

During this initialization of LTA, each of the increasing time constants (LongTermTime) is used LongTermTime times; that is, a LongTermTime value of one is used once, a LongTermTime value of two is used twice, a LongTermTime value of eight is used eight times, etc. . . . This protocol results in an averaging function that closely adapts to a baseline at first, but then becomes increasingly resistant to change. This allows a smoother transition from initialization phase to adaptive mode.

Until the final 32,768 LongTermTime constant is reached during LTA initialization, a "long term freeze" function is imposed to limit upward excursions of LTA due to exercise. This long term freeze is implemented by preventing the LTA from being updated (although the number of times at the time constant is incremented) for a given two-second interval if the SensorInterval value is at or below ADLRateInterval and MV High Intervention is not in progress.

Scaling Factor Autoinitialization

Upon implant, the ScalingFactor used to calibrate ACTIVITY COUNT values with MV COUNT values is initially set to a value which allows a predetermined patient activity level (e.g., 3 to 5 above-threshold peaks per second in the activity sensor signal) to drive the SensorRate near the ADL rate. ScalingFactor adjustments then occur each day, to match or calibrate ACTIVITY COUNT values to MV COUNT values, as will be hereinafter described in greater detail.

Daily Rate Response Operation

Daily rate response operation of device 10 includes updating a long-term sensor rate histogram, optimizing rate response therapy, and rescaling sensor indices.

The long-term sensor rate histogram is the sensor rate histogram available from device 10 through interrogation by an external programming device, e.g., at patient follow-up sessions at a clinic. Rescaling sensor indices involves adjustment of a ScalingFactor value, the multiplier used to put ActivityCounts on the same scale as MVCounts. Following completion of rate response initialization, when calculation of SensorInterval is enabled, Rescaling is automatically enabled if it has not been programmed OFF. ScalingFactor is initially set to a value which allows for a predetermined frequency of activity counts (e.g., 3, 4, or 5 activity counts per second) to drive SensorRate to approximately the ADLRate. Scaling factor adjustments then occur each day, to match the range activity sensor counts to that of minute ventilation sensor counts.

Optimization is provided as a means for automatically adapting the rate transfer function to optimize rate response therapy. The optimization algorithm in accordance with the presently disclosed embodiment of the invention attempts to match the actual long-term sensor rate histogram to a desired sensor rate histogram using two (mostly) independent criteria. One set of criteria is targeted to high rate (HiR) behavior, while the other is target to ADL behavior. If the actual number of events at or above ADLRate falls outside of the desired range, then it is assumed that ADLCounts is either too small (response too aggressive) or too large (response not aggressive enough), and needs to be adjusted accordingly. Similarly, if the actual number of events at or above a specified High Rate falls outside a desired range, then it is assumed that URCounts is either too small or too large. The task of updating the long-term sensor rate histogram and performing optimization occurs once a day.

As for the SensorRate computation algorithm itself, there are a number of dynamically variable values and programmable parameters maintained in memory block 30 by CPU 32 for supporting the operations associated with optimization of rate response operation. These are summarized in the following Table 3:

TABLE 3

| NAME/ACRONIM | DESCRIPTION |
| --- | --- |
| Optimization | Set to enable automatic (chronic) adjustments to the rate transfer function (programmable to ON or OFF) |
| Optimize Criteria | Storage for user presentation from programmer |
| Rescaling | Set to enable automatic adjustments of ScalingFactor (programmable to ON or OFF) |
| ScalingFactor | Value by which ACTIVITY COUNTS are multiplied to put them on the same scale as MV COUNTS (programmable to 0 to 40) |
| MinADLREvents | The minimum number of two-second events that must be at or above ADLRate used by the SensorRate determination algorithm to maintain the current mapping of SensorCounts to ADLRate |
| MaxADLREvents | The maximum number of two-second events that must be ADLRate or above used by the SensorRate determination algorithm to maintain the current mapping of SensorCounts to ADLRate |
| MinHiREvents | The minimum number of two-second events that must be at high rates used by the SensorRate determination algorithm to maintain current mapping of SensorCounts to UpperSensorRate |
| MaxHiREvents | The maximum number of two-second events that must be at high rates used by the SensorRate determination algorithm to maintain current mapping of SensorCounts to UpperSensorRate |
| DeltaADL | The amount that SensorCount mapping to ADLRate can change due to optimization (programmable to 0.8, 1.6, 3 or 6% of ADLCounts -- encoded as 4, 5, 6, or 7 in the formulas in the following Table 4) |
| DeltaMax | The amount that SensorCount mapping to UpperSensorRate can change due to optimization (programmable to 0.8, 1.6, 3, or 6% of URCounts) |
| ADLWidth | Fraction of URCounts that ADLWidthCounts represents |
| HiRinterval | The largest interval included in high rate behavior |
| ADLRate | Desired rate to achieve during daily activities (programmable to 40 to 180 BPM) |
| UpperSensorRate | The maximum value that SensorRate can achieve (programmable to 80 to 180 BPM) |
| ReinitHistory | Set to cause the long-term sensor rate distribution to be restarted |

As noted above, device 10 uses predefined criteria to determine the desired sensor rate distribution. As used herein, "sensor rate distribution" refers to the collection of data which reflects how many pacing pulses were delivered at each of the possible rates in the SensorRate range. In one embodiment, CPU 32 defines a "bin" (e.g., a memory location in memory block 30) for each possible pacing rate within the SensorRam range. The value in each bin reflects the number of pulses delivered at the SensorRate associated with that bin. The optimization criteria may be adjusted by the physician to customize the desired sensor rate distribution for a particular patient.

Each day the day's SensorRate distribution is added to the long-term distribution using a weighted averaging scheme. (If ReinitHistory is set, the long term distribution is cleared, and no optimization occurs.)

Twenty-four hours after (re)initialization, a single day's distribution becomes the long-term distribution. After this, a binary increasing averaging constant is used, until the final history constant (HistoryTime) of eight is reached.

Each "bin" stores a value LongTermEvents, for which the update equation is given by the following:

LongTermEvents = LongTermEvents +

$$INT\left(\frac{(\text{DailyEvents} \times 256) - \text{LongTermEvents}}{\text{HistoryTime}}\right)$$

where HistoryTime increases binarily to eight.

The long term distribution is preferably available for interrogation by an external programing/diagnostic unit.

In the same manner as the long-term distribution of LongTermEvent values is maintained, daily and long-term events at and below the ADLRateInterval and at and below HighRateInterval are maintained. These events are compared to desired ranges to determine whether or not the rate-response transfer function needs adjustment. (Expressing the desired range in terms of events is equivalent to expressing it in percentage of total events because the number of total events remains constant.)

High-rate behavior is evaluated by comparing the daily and long-term events to

HiREvents =

$$HiREvents + INT\left(\frac{(\text{Daily}HiR\text{Events} \times 256) - HiR\text{Events}}{\text{HistoryTime}}\right)$$

the desired range, MinHiREvents to MaxHiREvents. If the events fall below this range, this indicates a need to decrease the SensorCounts value that is mapped to the UpperSensorRate. If the events fall above this range, this indicates a need to increase the SensorCounts value that is mapped to the UpperSensorRate. The ADL behavior is handled in the same manner.

The following Table 4 shows the action taken based upon long term and daily ADL and high rate (HiR) and findings. In Table 4, the values in the "Action" column represent values used to compute updated ADLCount and URCounts values in accordance with equations to be set forth below.

TABLE 4

| LONG TERM | DAILY | ADL ACTION HiR ACTION | EFFECTIVE CHANGE |
|---|---|---|---|
| OK | — | 0 | None |
| Increase | Increase | DeltaADL − 2 | $1/2^{(\text{DeltaADL}-2)}$ of ADLCounts |
|  |  | DeltaMax − 2 | $1/2^{(\text{DeltaMax}-2)}$ of URCounts |
| Increase | OK | DeltaADL − 1 | $1/2^{(\text{DeltaADL}-1)}$ of ADLCounts |
|  |  | DeltaMax − 1 | $1/2^{(\text{DeltaMax}-1)}$ of URCounts |
| Increase | Decrease | 0 | None |
| Decrease | Increase | 0 | None |
| Decrease | OK | −DeltaADL | $1/2^{(\text{DeltaADL})}$ of ADLCounts |
|  |  | −DeltaMax | $1/2^{(\text{DeltaMax})}$ of URCounts |
| Decrease | Decrease | −(DeltaADL − 1) | $1/2^{(\text{DeltaADL}-1)}$ of ADLCounts |
|  |  | −(DeltaMax − 1) | $1/2^{(\text{DeltaMax}-1)}$ of URCounts |

The updating equation for ADLRate events, performed every 24 hours, is as follows:

ADLREvents = ADLREvents +

$$INT\left(\frac{(\text{Daily } ADL^R \text{ Events} \times 256) - ADLR\text{Events}}{\text{HistoryTime}}\right)$$

In addition to the actions identified in Table 4 above, there are three additional actions which may be taken in connection with ADL operation within a predetermined period of time (e.g., ten days) after (re)initialization of history. These actions, taken when both long-term and daily histories indicated a need for decrease, are as follows:

$$ADL\text{Action} = \begin{cases} -2, & \text{if MaxLimited}MV \leq \left(ADL\text{Counts} - \frac{ADL\text{Counts}}{4}\right) \\ -3, & \text{if}\left(ADL\text{Counts} - \frac{ADL\text{Counts}}{4}\right) < \text{MaxLimited}MV < ADL\text{Counts} \\ -4, & \begin{array}{l}\text{if (Daily}ADLR\text{Events} \times 2 \leq \text{Min}ADLR\text{Events) AND} \\ ((\text{MaxLimited}MV \leq ADL\text{Counts}) \text{ OR } (RR\text{SensorIsActivity}))\end{array} \end{cases}$$

Similarly, the updating equation for high-rate events, also performed every 24 hours, is as follows:

where RRSensorIsActivity is a boolean variable which is "true" if only activity sensing is enabled.

Similarly, there are three additional actions which may be taken in connection with HiR operation within a predetermined period of time (e.g., ten days) after (re)initialization of history, as follows:

$$HiRAction = \begin{cases} -2, & \text{if MaxLimited}MV \leq \left(ADL\text{Counts} - \frac{ADL\text{Counts}}{4}\right) \\ -3, & \text{if}\left(ADL\text{Counts} - \frac{ADL\text{Counts}}{4}\right) < \text{MaxLimited}MV < ADL\text{Counts} \\ -4, & \text{if (Daily}ADLR\text{Events} \times 2 \leq \text{Min}ADLR\text{Events)} \land \\ & (\text{Daily}ADLR\text{Events} \times 2 \leq \text{Min}ADLR\text{Events})) \land \\ & ((\text{MaxLimited}MV \geq ADL\text{Counts}) \lor (RR\text{SensorIsActivity})) \end{cases}$$

The equation for changing the Sensor3Counts mapped to UpperSensorRate (i.e., the equation for URCounts) is as follows:

$$URCounts = \begin{cases} UR\text{Counts} + \frac{UR\text{Counts}}{2^{HiRAction}}, & \text{if } HiRAction > 0 \\ UR\text{Counts} - \frac{UR\text{Counts}}{2^{|HiRAction|}}, & \text{if } HiRAction < 0 \end{cases}$$

Similarly, if the actual amount at ADLRate or above falls below MinADLREvents, or is above MaxADLREvents, the Sensor3Counts mapped to ADLRate is decreased, or increased, as given by the following:

Either or both adjustments (i.e., ADLCounts or URCounts) are possible each day. Adjustment of ADLCounts requires recalculation of both slopes of the rate transfer function and any parameters dependent upon ADLCounts. Adjustment of URCounts $ADL\text{Counts} =$ $$\begin{cases} ADL\text{Counts} + \frac{ADL\text{Counts}}{2^{ADLAction}}, & \text{if } ADLAction > 0 \\ ADL\text{Counts} - \frac{ADL\text{Counts}}{2^{|ADLAction|}}, & \text{if } ADLAction > 0 \end{cases}$$

requires recalculation of the upper slope of the rate transfer function and any parameters dependent upon URCounts, including ADLWidthCounts. If both adjustments are needed, the ADLCounts adjustment is performed first.

The relationship between the MV sensor range and the activity sensor range is expected to be relatively constant over time, but is preferably evaluated daily to ensure that any changes over time are reflected in the scaling.

Two values, MaxMV and MaxSActAverage are updated every two seconds. Each day, they are compared. ScalingFactor is then adjusted as given in the following equation:

$ScalingFactor =$ $$\begin{cases} ScalingFactor - 1, & \text{if MaxSActAverage} \leq \text{MaxLimited}MV + 1 \\ ScalingFactor + 1, & \text{if MaxSActAverage} < \text{MaxLimited}MV \\ ScalingFactor, & \text{otherwise} \end{cases}$$

If ScalingFactor was changed, MaxSActAverage is set to MaxMV.

Rescaling can occur in the same day as an optimization adjustment. In this case, MaxMV is decreased by $1/64$, to allow for decreases in the MV signal over time.

From the foregoing detailed description of a specific embodiment of the invention, it should be apparent that a novel method and apparatus for rate-responsive cardiac pacing has been disclosed. Although a specific embodiment of the invention has been described herein in some detail, this has been done solely for the purpose of illustrating the invention in various of its aspects, and it is to be understood that the foregoing description does not limit the scope of the invention. It is contemplated that various substitutions, alterations, and/or modifications to the embodiment of the invention disclosed herein, including but not limited to those implementation options specifically noted herein, may be made to the invention without departing from the spirit and scope of the invention as defined in the appended claims, which follow.

What is claimed is:

1. A cardiac pacemaker, comprising:

a stimulating pulse generator for producing a cardiac stimulating pulse in response to a trigger signal;

a first sensing circuit in said pacemaker for detecting cardiac electrical signals;

a cardiac pacing lead having at least one conductor and having at least one electrode in electrical contact at one end thereof to a patient's heart, for conducting said cardiac stimulating pulse from said pulse generator to said patient's heart and for conducting cardiac electrical signals to said first sensing circuit;

an impedance sensing circuit, coupled to said lead, for generating an electrical impedance signal whose level reflects said patient's minute ventilation level;

an activity sensing circuit adapted to generate an electrical activity signal whose level reflects said patient's activity level;

a rate determination circuit, coupled to receive impedance level signals from said impedance sensing circuit and to receive said activity level signals from said activity sensing circuit, said rate determination circuit periodically deriving a new rate value as a function of a current rate value and of said activity signal level and said impedance signal level, said new rate value being within a rate range defined by predetermined lower and upper limits, said activity signal level having greater influence than said impedance signal on said rate value derivation when said current rate value is in a lower segment of said rate range, and said impedance signal having greater influence than said activity signal on said rate value derivation when said current rate value is in an upper segment of said rate range;

a control circuit, coupled to said pulse generator, said first sensing circuit, and said rate determination circuit, for generating a sequence of said trigger signals at a rate which varies in accordance with said periodically derived new rate value.

2. A pacemaker system in accordance with claim 1, wherein said activity sensing circuit includes a piezoelectric transducer for producing a generally pulsatile electrical output signal reflecting said patient's physical activity level.

3. A pacemaker system in accordance with claim 1, wherein said impedance sensing circuit comprises:

an excitation current generator coupled to said lead, for producing excitation pulses to be applied to said patient's heart via said at least one electrode in said lead and through a second electrode;

a voltage differential detection circuit, coupled to said at least one electrode and to a second electrode, for measuring voltage differentials between said at least one electrode for delivery said excitation pulses to said patient's heart and said second electrode.

4. A cardiac pacemaker, comprising:

a stimulating pulse generator for producing a cardiac stimulating pulse in response to a trigger signal;

a first sensing circuit in said pacemaker for detecting cardiac electrical signals;

a cardiac pacing lead having at least one conductor and having at least one electrode in electrical contact at one end thereof to a patient's heart, for conducting said cardiac stimulating pulse to said patient's heart and for conducting cardiac electrical signals to said first sensing circuit;

an impedance sensing circuit, coupled to said lead, for periodically generating a minute ventilation count value whose magnitude reflects said patient's minute ventilation level;

an activity sensing circuit adapted to periodically generate an activity count value whose magnitude reflects said patient's activity level;

a rate determination circuit, coupled to receive impedance level signals from said impedance sensing circuit and to receive activity level signals from said activity sensing circuit, said rate determination circuit periodically deriving a new rate value in accordance with a rate transfer function having a current rate value and said minute ventilation count value and said activity count value as input parameters, said rate transfer function being defined to constrain said rate value to lie within a rate range defined by predetermined lower and upper limits, said rate transfer function being further defined such that said activity value has greater influence than said impedance level signal on rate values derived in accordance with said rate transfer function when said current rate value is in a lower segment of said rate range, and said impedance level signal having greater influence than said activity count value on rate values derived in accordance with said rate transfer function when said current rate value is in an upper segment of said rate range;

a control circuit, coupled to said pulse generator and to said rate determination circuit, for generating a sequence of said trigger signals at a rate which varies in accordance with said periodically derived rate value.

5. The system in accordance with claim 4, wherein said rate transfer function is further defined to utilize at least one scaling factor for determining relative influence of said activity count value and said impedance value on rate values determined in accordance with said transfer function.

6. The system in accordance with claim 4, wherein said rate determination circuit further includes a histogram memory circuit for storing data reflecting said system's rate response operation over a predetermined period of time.

7. The apparatus in accordance with claim 6, wherein said rate response operation reflected by said histogram data is periodically compared to predetermined desired rate response data, and wherein said at least one scaling factor is periodically adjusted based upon the outcome of said comparison, such that rate response operation of said system is periodically optimized.

8. A pacemaker in accordance with claim 4, wherein said activity sensing circuit comprises:

a piezoelectric transducer for producing a generally pulsatile activity sensor output signal reflecting said patient's level of physical activity;

a threshold detection circuit, for asserting an activity detection output signal in response to any excursion of said generally pulsatile piezoelectric transducer output signal above a predetermined threshold; and a counting circuit, responsive to said assertion of said activity detection output signal to increment a count value, said count value being periodically supplied to said rate determination circuit as said activity level signal.

9. A pacemaker in accordance with claim 4, wherein said impedance sensing circuit comprises:

an excitation pulse generating circuit, coupled to said lead, for producing current excitation pulses to be applied to an area generally in said patient's thoracic region;

a voltage differential detection circuit, coupled to said at least one electrode via said lead and coupled to a second electrode disposed generally in said patient's thoracic region, said voltage detection circuit producing an impedance signal whose level reflects voltage differentials between said at least one electrode and said second electrode resulting from said application of said excitation pulses;

a delta modulator circuit connected to receive said impedance level signal, for periodically deriving a delta modulator output value whose magnitude reflects any change in said impedance signal level since said delta modulator derived a previous delta modulator output value;

an accumulator, for maintaining a sum of successive ones of said delta modulator output values and periodically supplying said sum to said rate determination circuit as said minute ventilation level signal.

10. A pacemaker system in accordance with claim 4, further comprising a digital memory unit for storing a program of processor instructions, and wherein said control circuit comprises a processor for executing said stored program of processor instructions to implement said rate transfer function.

11. A method of operating a rate-responsive cardiac pacemaker system adapted to vary its pacing rate within a rate range defined by predetermined upper and lower limits, said method comprising the steps of:

(a) monitoring a first physiologic parameter of a patient, where said first physiologic parameter's level is known to be indicative of said patient's metabolic demand for increased cardiac output;

(b) monitoring a second physiologic parameter of said patient, where said second physiologic parameter's level is known to be indicative of said patient's metabolic demand for increased cardiac output;

(c) periodically deriving a rate value in accordance with a rate transfer function applied to values reflecting said first and second physiologic parameter levels and to a value reflecting a present pacing rate value, said rate transfer function being defined such that when said present rate value lies within a lower segment of said rate range, said first parameter's level dominates over said second parameter's level in said rate derivation, and such that when said present rate value lies within an upper segment of said rate range, said second parameter's level dominates over said first parameter's level in said rate derivation.

12. A method in accordance with claim 11, wherein said first physiologic parameter is said patient's activity level, and wherein said step (a) of monitoring said first physiologic parameter comprises monitoring an electrical signal from a piezoelectric transducer.

13. A method in accordance with claim 11, wherein said second physiologic parameter is said patient's minute ventilation level, and wherein said step (b) of monitoring said second physiologic parameter comprises the steps of:

(c) delivering excitation pulses in the region of said patient's heart;

(d) monitoring a variations in a voltage differential between at least two electrodes disposed generally in the region of said patient's heart, said voltage differential variations resulting from said delivery of said excitation pulses.

14. A method of varying a cardiac pacemaker's pacing rate, within a range defined by predetermined upper and lower limits, in response to variations in a first sensed physiologic parameter value and to variations in a second sensed physiologic parameter value, said method comprising the steps of:

(a) defining a rate transfer function in terms of a current rate value, said first physiologic parameter value multiplied by a first weighting factor, and said second physiologic parameter value multiplied by a second parameter weighting factor, wherein said first weighting factor decreases to zero as said current rate value increases and wherein said second weighting factor increases from zero as said current rate value increases;

(b) periodically recomputing a new rate value in accordance with said rate transfer function.

15. A method in accordance with claim 14, wherein said first sensed physiologic parameter value is a count value whose magnitude reflects a patient's activity level as sensed by a piezoelectric transducer, and wherein said second sensed physiologic parameter values is a count value whose magnitude reflects cardiac impedance in said patient.

16. A method in accordance with claim 14, further comprising the steps of:

(e) periodically updating at least one histogram data value in accordance with current rate response operation of said system, such that said histogram data value reflects the rate response operation of said system over a predetermined history time;

(f) periodically comparing said at least one histogram value to predetermined desired values; and (g) periodically adjusting said first and second weighting factors in accordance with the outcome of said comparison in step (f), such that rate response operation of said system is optimized.

17. A cardiac pacemaker system comprising:

a stimulating pulse generator for producing a cardiac stimulating pulse in response to a trigger signal;

a first sensing circuit for detecting electric signals;

a cardiac pacing electrode coupled to the pulse generator in electrical contact to a patient's heart for providing cardiac stimulating pulses to said patient's heart therethrough and for providing cardiac electrical signals to said first sensing circuit;

an impedance sensing circuit coupled to said electrode for generating an electrical impedance signal whose level reflects said patient's minute ventilation level;

an activity sensing circuit adapted to generate an electrical activity signal whose level reflects said patient's activity level;

a sensor combination circuit for receiving output from said impedance sensing circuit and said activity sensing circuit and providing a blended value as an output signal level value indicative of a combination of said received output signal values, said impedance sensing circuit output value having a greater influence than said activity signal value on said blended output value when a current rate value is in a lower segment of a rate change but a lesser influence when the current rate value is in a upper segment of said rate range;

a rate determination circuit coupled to said sensor combination circuit for periodically deriving a new rate value as a function of a current rate and of said blended value;

a control circuit coupled to said pulse generator, said first sensing circuit, and said rate determination circuit for generating a sequence of said trigger signals at a rate which varies in accordance with said periodically derived rate value.

18. A device as set forth in claim 17 wherein said sensor combination circuit combines said impedance sensing circuit output value (DMV) and said activity sensor circuit output (SActCnt) as follows:

when DMV<SActCnt there are the output signal level is directly correlated to a combine value, said combine value being a function of the current rate interval, times the SActCnt plus the DMV times the sum of 1 minus said combine value, and when DM≧SActCnt, the output signal level is directly correlated to the DMV.

* * * * *

UNITED STATES PATENT AND TRADEMARK OFFICE
CERTIFICATE OF CORRECTION

PATENT NO.  : 5,562,711
DATED       : October 8, 1996
INVENTOR(S) : Yerich et al.

It is certified that error appears in the above-identified patent and that said Letters Patent is hereby corrected as shown below:

Column 6,
Line 36, "Mealtronic" should read -- Medtronic --
Line 65, "modelled" should read -- modeled --

Column 7,
Line 10, "may encodes" should read -- may encode --
Line 22, "Mealtronic" should read -- Medtronic --

Column 8,
Line 46, "PING" should read -- RING --

Column 10,
Line 44, "A" should read -- --
Line 47, "A" should read -- --

Column 13, Table 2:
Line 38, "ADLRateinterval" should read -- ADLRateInterval --
Line 50, "1 2," should read -- 12 --
Line 71, "HighRatecrossCheck" should read -- HighRateCrossCheck --

Column 15, Table 2:
Line 4, "1 2.5, 25, 50 or 1 00%" should read -- 12.5, 25, 50 or 100% --
Line 12, "LowerRateinterval' should read -- LowerRateInterval --

Column 16,
Line 44, ".greater" should read -- greater --

Column 17,
Line 9, "approximately hours" should read -- approximately 18 hours --
Line 16, "$LSTA=_{MIN}$" should read -- LSTA = MIN --

Column 18,
Line 32, "designate" should read -- designated --

Column 19,
Line 60, start a new paragraph after the word "dominant."

UNITED STATES PATENT AND TRADEMARK OFFICE
CERTIFICATE OF CORRECTION

PATENT NO. : 5,562,711
DATED : October 8, 1996
INVENTOR(S) : Yerich et al.

It is certified that error appears in the above-identified patent and that said Letters Patent is hereby corrected as shown below:

Column 20,
Line 51, "unites" should read -- units --
Line 54, "CSlope 1" should read -- CSlope1 --

Column 21,
Line 19, "Sensor3Coums" should read -- Sensor3Counts --

Column 24,
Line 27, "increases" should read -- increases. --
Line 35, "Sensodnterval" should read -- SensorInterval --

Column 26,
Line 2, "High." should read -- High). --

Column 28,
Line 7, "ACRONIM" should read -- ACRONYM --
Line 38, table 3: "HiRinterval" should read -- HiRInterval --
Line 53, "SensorRam" should read -- SensorRate --

Column 29,
Line 10, "programing" should read -- programming --
Line 41, in equation: "$ADL^R Events$" should read -- $ADLREvents$ --

Column 30,
Line 27, table 4: "(DeltsMax-1)" should read -- (DeltaMax-1) --
Line 54, in equation: "$\leq ADLCounts$" should read -- $\geq ADLCounts$ --

Column 31,
Line 51, in equation: "$\leq$" should read -- $\geq$ --

UNITED STATES PATENT AND TRADEMARK OFFICE
CERTIFICATE OF CORRECTION

PATENT NO. : 5,562,711
DATED : October 8, 1996
INVENTOR(S) : Yerich et al.

It is certified that error appears in the above-identified patent and that said Letters Patent is hereby corrected as shown below:

Column 36, claim 17,
Line 25, "a current" should read -- the current --

Column 36, claim 18,
Line 46, "DM$\geq$ "should read -- DMV$\geq$ --

Signed and Sealed this

Eighteenth Day of September, 2001

*Attest:*

*Attesting Officer*

NICHOLAS P. GODICI
*Acting Director of the United States Patent and Trademark Office*